US012797462B2

(12) United States Patent
Yu et al.

(10) Patent No.: US 12,797,462 B2
(45) Date of Patent: Nov. 17, 2026

(54) FUSION GENE, RECOMBINANT NOVEL CORONAVIRUS HIGH-EFFICIENCY IMMUNE DNA VACCINE, CONSTRUCTION METHOD AND USE THEREOF

(71) Applicant: Aurora Genevac Biotech Co., Ltd., Beijing (CN)

(72) Inventors: Jiyun Yu, Beijing (CN); Yu Wang, Beijing (CN); Weiwei Song, Beijing (CN); Jinqi Yan, Beijing (CN); Qiang Xu, Beijing (CN); Yu Xia, Beijing (CN); Yachao Liu, Beijing (CN); Kun Gao, Beijing (CN); Chuang-Jiun Chiou, Beijing (CN)

(73) Assignee: Aurora Genevac Biotech Co., Ltd., Beijing (CN)

( * ) Notice: Subject to any disclaimer, the term of this patent is extended or adjusted under 35 U.S.C. 154(b) by 895 days.

(21) Appl. No.: 18/013,663

(22) PCT Filed: Nov. 19, 2021

(86) PCT No.: PCT/CN2021/131786
§ 371 (c)(1),
(2) Date: Dec. 29, 2022

(87) PCT Pub. No.: WO2022/105880
PCT Pub. Date: May 27, 2022

(65) Prior Publication Data

US 2023/0355742 A1 Nov. 9, 2023

(30) Foreign Application Priority Data

Nov. 20, 2020 (CN) ......................... 202011310160.8

(51) Int. Cl.

| | |
|---|---|
| ***A61K 39/215*** | (2006.01) |
| ***A61K 39/00*** | (2006.01) |
| ***A61P 37/04*** | (2006.01) |
| ***C12N 15/62*** | (2006.01) |
| ***C12N 15/63*** | (2006.01) |
| ***C12N 15/66*** | (2006.01) |

(52) U.S. Cl.
CPC ............ *A61K 39/215* (2013.01); *A61P 37/04* (2018.01); *A61K 2039/53* (2013.01); *C12N 15/62* (2013.01); *C12N 15/625* (2013.01); *C12N 15/63* (2013.01); *C12N 15/66* (2013.01)

(58) Field of Classification Search
CPC .............. A61K 39/215; A61K 2039/53; A61K 39/12; A61P 37/04; A61P 31/14; C07K 2319/00; C07K 14/28; C07K 14/005; C07K 14/33; C07K 14/70578; C07K 2319/50; C07K 2319/55; C12N 2710/10322; C12N 2770/20022; C12N 2770/20034; C12N 2770/36143; C12N 2795/10122; C12N 2840/203; Y02A 50/30
See application file for complete search history.

(56) References Cited

U.S. PATENT DOCUMENTS

| | | | | |
|---|---|---|---|---|
| 2016/0281106 | A1* | 9/2016 | Kim | C12N 15/85 |
| 2020/0061185 | A1 | 2/2020 | Graham et al. | |
| 2023/0108894 | A1* | 4/2023 | Stewart-Jones | A61P 31/14 424/221.1 |
| 2023/0257425 | A1* | 8/2023 | Kwon | C07K 14/005 424/192.1 |
| 2023/0302120 | A1* | 9/2023 | Chopra | A61K 39/12 |
| 2023/0302121 | A1* | 9/2023 | Niazi | C12N 1/16 |
| 2023/0346914 | A1* | 11/2023 | Stewart-Jones | A61K 39/215 |

FOREIGN PATENT DOCUMENTS

| | | | | |
|---|---|---|---|---|
| CN | 105343874 A | | 2/2016 | |
| CN | 111217917 A | | 6/2020 | |
| CN | 111228475 A | | 6/2020 | |
| CN | 111499765 A | | 8/2020 | |
| CN | 111662389 A | | 9/2020 | |
| CN | 111705006 A | | 9/2020 | |
| CN | 111821433 A | | 10/2020 | |
| CN | 112048007 A | | 12/2020 | |
| CN | 111939250 B | * | 7/2022 | A61K 39/12 |

(Continued)

OTHER PUBLICATIONS

Xia X. Domains and Functions of Spike Protein in Sars-Cov-2 in the Context of Vaccine Design. Viruses. Jan. 14, 2021;13(1):109. (Year: 2021).*
Lan J, Ge J, Yu J, Shan S, Zhou H, Fan S, Zhang Q, Shi X, Wang Q, Zhang L, Wang X. Structure of the SARS-CoV-2 spike receptor-binding domain bound to the ACE2 receptor. Nature. May 2020;581(7807):215-220. Epub Mar. 30, 2020. (Year: 2020).*
Tai W, He L, Zhang X, Pu J, Voronin D, Jiang S, Zhou Y, Du L. Characterization of the receptor-binding domain (RBD) of 2019 novel coronavirus: implication for development of RBD protein as a viral attachment inhibitor and vaccine. Cell Mol Immunol. Jun. 2020;17(6):613-620. Epub Mar. 19, 2020. (Year: 2020).*
Yu J. et al., "DNA Vaccine Protection Against SARS-CoV-2 in Rhesus Macaques", Science 369:806-812 (2020) (cited in JP OA).

(Continued)

*Primary Examiner* — Rachel B Gill
(74) *Attorney, Agent, or Firm* — Scully, Scott, Murphy & Presser, P.C.

(57) ABSTRACT

A fusion gene, a recombinant novel coronavirus high-efficiency immune DNA vaccine, a construction method and use thereof are provided. The immune DNA vaccine ZD-nCor19 provided herein uses RBD protein, residues 301-538 in the S2 subunit and residues 138-369 in the N protein of the novel coronavirus as target antigens, and has specific immune synergism molecules introduced at suitable positions, and thus can simultaneously efficiently induce humoral immunity and cellular immunity, and can avoid safety problems associated with ADE that may be generated by the full-length S protein and the full-length N protein, thereby achieving dual effects of prevention and treatment. The vaccine can be used as a safe, efficient and stable vaccine variety against novel coronavirus infection.

15 Claims, 6 Drawing Sheets

Specification includes a Sequence Listing.

(56) References Cited

FOREIGN PATENT DOCUMENTS

| | | | | | |
|---|---|---|---|---|---|
| EP | 4 166 649 | A1 | | 4/2023 | |
| WO | 2021-198376 | A1 | | 10/2021 | |
| WO | 2022/052984 | A1 | | 3/2022 | |
| WO | WO-2022269003 | A1 | * | 12/2022 | ........... C07K 14/005 |

OTHER PUBLICATIONS

Japanese Office Action dated May 7, 2024 received in Japanese Patent Application No. 2023-514153, together with an English-language translation.
Rafael Assis et al."Distinct SARS-CoV-2 antibody reactivity patterns elicited by natural infection and mRNA vaccination", NPJ Vaccines, vol. 6, No. 1, Nov. 4, 2021 (Nov. 4, 2021), ISSN:2059-0105, see pp. 1-10.
International Search Report dated Feb. 22, 2022 issued in PCT/CN2021/131786.
Extended European Search Report dated Mar. 10, 2025 received in European Application No. 21 894 027.8.

* cited by examiner

SEQUENCE LISTING

<160> NUMBER OF SEQ ID NOS: 16

<210> SEQ ID NO 1
<211> LENGTH: 14441
<212> TYPE: DNA
<213> ORGANISM: Artificial Sequence
<220> FEATURE:
<223> OTHER INFORMATION: Polynucleotide of the pZDVac-CCCPO plasmid

<400> SEQUENCE: 1

```
gcttactggc ttatcgaaat taatacgact cactataggg agaccggaag cttgaattca     60

tggcggatgt gtgacataca cgacgccaaa agattttgtt ccagctcctg ccacctccgc    120

tacgcgagag attaaccacc cacgatggcc gccaaagtgc atgttgatat tgaggctgac    180

agcccattca tcaagtcttt gcagaaggca tttccgtcgt tcgaggtgga gtcattgcag    240

gtcacaccaa atgaccatgc aaatgccaga gcattttcgc acctggctac caaattgatc    300

gagcaggaga ctgacaaaga cacactcatc ttggatatcg gcagtgcgcc ttccaggaga    360

atgatgtcta cgcacaaata ccactgcgta tgccctatgc gcagcgcaga agaccccgaa    420

aggctcgtat gctacgcaaa gaaactggca gcggcctccg ggaaggtgct ggatagagag    480

atcgcaggaa aaatcaccga cctgcagacc gtcatggcta cgccagacgc tgaatctcct    540

accttttgcc tgcatacaga cgtcacgtgt cgtacggcag ccgaagtggc cgtataccag    600

gacgtgtatg ctgtacatgc accaacatcg ctgtaccatc aggcgatgaa aggtgtcaga    660

acggcgtatt ggattgggtt tgacaccacc ccgtttatgt ttgacgcgct agcaggcgcg    720

tatccaacct acgccacaaa ctgggccgac gagcaggtgt tacaggccag gaacatagga    780

ctgtgtgcag catccttgac tgagggaaga ctcggcaaac tgtccattct ccgcaagaag    840

caattgaaac cttgcgacac agtcatgttc tcggtaggat ctacattgta cactgagagc    900

agaaagctac tgaggagctg gcacttaccc tccgtattcc acctgaaagg taaacaatcc    960

tttacctgta ggtgcgatac catcgtatca tgtgaagggt acgtagttaa gaaaatcact   1020

atgtgccccg gcctgtacgg taaaacggta gggtacgccg tgacgtatca cgcggaggga   1080

ttcctagtgt gcaagaccac agacactgtc aaaggagaaa gagtctcatt ccctgtatgc   1140

acctacgtcc cctcaaccat ctgtgatcaa atgactggca tactagcgac cgacgtcaca   1200

ccggaggacg cacagaagtt gttagtggga ttgaatcaga ggatagttgt gaacggaaga   1260

acacagcgaa acactaacac gatgaagaac tatctgcttc cgattgtggc cgtcgcattt   1320

agcaagtggg cgagggaata caaggcagac cttgatgatg aaaaacctct gggtgtccga   1380
```

-continued

```
gagaggtcac ttacttgctg ctgcttgtgg gcatttaaaa cgaggaagat gcacaccatg   1440
tacaagaaac cagacaccca gacaatagtg aaggtgcctt cagagtttaa ctcgttcgtc   1500
atcccgagcc tatggtctac aggcctcgca atcccagtca gatcacgcat taagatgctt   1560
ttggccaaga agaccaagcg agagttaata cctgttctcg acgcgtcgtc agccagggat   1620
gctgaacaag aggagaagga gaggttggag gccgagctga ctagagaagc cttaccaccc   1680
ctcgtcccca tcgcgccggc ggagacggga gtcgtcgacg tcgacgttga agaactagag   1740
tatcacgcag gtgcaggggt cgtggaaaca cctcgcagcg cgttgaaagt caccgcacag   1800
ccgaacgacg tactactagg aaattacgta gttctgtccc cgcagaccgt gctcaagagc   1860
tccaagttgg cccccgtgca ccctctagca gagcaggtga aaataataac acataacggg   1920
agggccggcc gttaccaggt cgacggatat gacggcaggg tcctactacc atgtggatcg   1980
gccattccgg tccctgagtt tcaagctttg agcgagagcg ccactatggt gtacaacgaa   2040
agggagttcg tcaacaggaa actataccat attgccgttc acggaccgtc gctgaacacc   2100
gacgaggaga actacgagaa agtcagagct gaaagaactg acgccgagta cgtgttcgac   2160
gtagataaaa aatgctgcgt caagagagag gaagcgtcgg gtttggtgtt ggtgggagag   2220
ctaaccaacc ccccgttcca tgaattcgcc tacgaagggc tgaagatcag gccgtcggca   2280
ccatataaga ctacagtagt aggagtcttt ggggttccgg gatcaggcaa gtctgctatt   2340
attaagagcc tcgtgaccaa acacgatctg gtcaccagcg gcaagaagga gaactgccag   2400
gaaatagtca acgacgtgaa gaagcaccgc ggactggaca tccaggcaaa aacagtggac   2460
tccatcctgc taaacgggtg tcgtcgtgcc gtggacatcc tatatgtgga cgaggctttc   2520
gcttgccatt ccggtactct gctagcccta attgctcttg ttaaacctcg gagcaaagtg   2580
gtgttatgcg gagaccccaa gcaatgcgga ttcttcaata tgatgcagct taaggtgaac   2640
ttcaaccaca acatctgcac tgaagtatgt cataaaagta tatccagacg ttgcacgcgt   2700
ccagtcacgg ccatcgtgtc tacgttgcac tacggaggca agatgcgcac gaccaacccg   2760
tgcaacaaac ccataatcat agacaccaca ggacagacca agcccaagcc aggagacatc   2820
gtgttaacat gcttccgagg ctgggtaaag cagctgcagt tggactaccg tggacacgaa   2880
gtcatgacag cagcagcatc tcagggcctc acccgcaaag ggtatacgc cgtaaggcag   2940
aaggtgaatg aaaatccctt gtatgcccct gcgtcggagc acgtgaatgt actgctgacg   3000
cgcactgagg ataggctggt gtggaaaacg ctggccggcg atccctggat taaggtccta   3060
tcaaacattc cacagggtaa ctttacggcc acattggaag aatggcaaga agaacacgac   3120
aaaataatga aggtgattga aggaccggct gcgcctgtgg acgcgttcca gaacaaagcg   3180
aacgtgtgtt gggcgaaaag cctggtgcct gtcctggaca ctgccggaat cagattgaca   3240
gcagaggagt ggagcaccat aattacagca tttaaggagg acagagctta ctctccagtg   3300
gtggccttga atgaaatttg caccaagtac tatggagttg acctggacag tggcctgttt   3360
tctgccccga aggtgtccct gtattacgag aacaaccact gggataacag acctggtgga   3420
aggatgtatg gattcaatgc cgcaacagct gccaggctgg aagctagaca taccttcctg   3480
aaggggcagt ggcatacggg caagcaggca gttatcgcag aaagaaaaat ccaaccgctt   3540
tctgtgctgg acaatgtaat tcctatcaac cgcaggctgc cgcacgccct ggtggctgag   3600
tacaagacgg ttaaaggcag tagggttgag tggctggtca ataaagtaag agggtaccac   3660
gtcctgctgg tgagtgagta caacctggct ttgcctcgac gcagggtcac ttggttgtca   3720
```

-continued

```
ccgctgaatg tcacaggcgc cgataggtgc tacgacctaa gtttaggact gccggctgac   3780
gccggcaggt tcgacttggt ctttgtgaac attcacacgg aattcagaat ccaccactac   3840
cagcagtgtg tcgaccacgc catgaagctg cagatgcttg ggggagatgc gctacgactg   3900
ctaaaacccg gcggcagcct cttgatgaga gcttacggat acgccgataa aatcagcgaa   3960
gccgttgttt cctccttaag cagaaagttc tcgtctgcaa gagtgttgcg cccggattgt   4020
gtcaccagca atacagaagt gttcttgctg ttctccaact ttgacaacgg aaagagaccc   4080
tctacgctac accagatgaa taccaagctg agtgccgtgt atgccggaga agccatgcac   4140
acggccgggt gtgcaccatc ctacagagtt aagagagcag acatagccac gtgcacagaa   4200
gcggctgtgg ttaacgcagc taacgcccgt ggaactgtag gggatggcgt atgcagggcc   4260
gtggcgaaga aatggccgtc agcctttaag ggagaagcaa caccagtggg cacaattaaa   4320
acagtcatgt gcggctcgta ccccgtcatc cacgctgtag cgcctaattt ctctgccacg   4380
actgaagcgg aaggggaccg cgaattggcc gctgtctacc gggcagtggc cgccgaagta   4440
aacagactgt cactgagcag cgtagccatc ccgctgctgt ccacaggagt gttcagcggc   4500
ggaagagata ggctgcagca atccctcaac catctattca cagcaatgga cgccacggac   4560
gctgacgtga ccatctactg cagagacaaa agttgggaga agaaaatcca ggaagccata   4620
gacatgagga cggctgtgga gttgctcaat gatgacgtgg agctgaccac agacttggtg   4680
agagtgcacc cggacagcag cctggtgggt cgtaagggct acagtaccac tgacgggtcg   4740
ctgtactcgt actttgaagg tacgaaattc aaccaggctg ctattgatat ggcagagata   4800
ctgacgttgt ggcccagact gcaagaggca aacgaacaga tatgcctata cgcgctgggc   4860
gaaacaatgg acaacatcag atccaaatgt ccggtgaacg attccgattc atcaacacct   4920
cccaggacag tgccctgcct gtgccgctac gcaatgacag cagaacggat cgcccgcctt   4980
aggtcacacc aagttaaaag catggtggtt tgctcatctt ttccccctccc gaaataccat   5040
gtagatgggg tgcagaaggt aaagtgcgag aaggttctcc tgttcgaccc gacggtacct   5100
tcagtggtta gtccgcggaa gtatgccgca tctacgacgg accactcaga tcggtcgtta   5160
cgagggtttg acttggactg gaccaccgac tcgtcttcca ctgccagcga taccatgtcg   5220
ctacccagtt tgcagtcgtg tgacatcgac tcgatctacg agccaatggc tcccatagta   5280
gtgacggctg acgtacaccc tgaacccgca ggcatcgcgg acctggcggc agatgtgcat   5340
cctgaacccg cagaccatgt ggacctcgag aacccgattc ctccaccgcg cccgaagaga   5400
gctgcatacc ttgcctcccg cgcggcggag cgaccggtgc cggcgccgag aaagccgacg   5460
cctgccccaa ggactgcgtt taggaacaag ctgcctttga cgttcggcga ctttgacgag   5520
cacgaggtcg atgcgttggc ctccgggatt actttcggag acttcgacga cgtcctgcga   5580
ctaggccgcg cgggtgcata tattttctcc tcggacactg gcagcggaca tttacaacaa   5640
aaatccgtta ggcagcacaa tctccagtgc gcacaactgg atgcggtcga ggaggagaaa   5700
atgtacccgc caaaattgga tactgagagg gagaagctgt tgctgctgaa aatgcagatg   5760
cacccatcgg aggctaataa gagtcgatac cagtctcgca aagtggagaa catgaaagcc   5820
acggtggtgg acaggctcac atcgggggcc agattgtaca cgggagcgga cgtaggccgc   5880
ataccaacat acgcggttcg gtacccccgc cccgtgtact cccctaccgt gatcgaaaga   5940
ttctcaagcc ccgatgtagc aatcgcagcg tgcaacgaat acctatccag aaattaccca   6000
acagtggcgt cgtaccagat aacagatgaa tacgacgcat acttggacat ggttgacggg   6060
tcggatagtt gcttggacag agcgacattc tgcccggcga agctccggtg ctacccgaaa   6120
```

```
catcatgcgt accaccagcc gactgtacgc agtgccgtcc cgtcaccctt tcagaacaca   6180

ctacagaacg tgctagcggc cgccaccaag agaaactgca acgtcacgca aatgcgagaa   6240

ctacccacca tggactcggc agtgttcaac gtggagtgct tcaagcgcta tgcctgctcc   6300

ggagaatatt gggaagaata tgctaaacaa cctatccgga taaccactga gaacatcact   6360

acctatgtga ccaaattgaa aggcccgaaa gctgctgcct tgttcgctaa gacccacaac   6420

ttggttccgc tgcaggaggt tcccatggac agattcacgg tcgacatgaa acgagatgtc   6480

aaagtcactc cagggacgaa acacacagag gaaagaccca aagtccaggt aattcaagca   6540

gcggagccat tggcgaccgc ttacctgtgc ggcatccaca gggaattagt aaggagacta   6600

aatgctgtgt tacgccctaa cgtgcacaca ttgtttgata tgtcggccga agactttgac   6660

gcgatcatcg cctctcactt ccacccagga gacccggttc tagagacgga cattgcatca   6720

ttcgacaaaa gccaggacga ctccttggct cttacaggtt taatgatcct cgaagatcta   6780

ggggtggatc agtacctgct ggacttgatc gaggcagcct ttggggaaat atccagctgt   6840

cacctaccaa ctggcacgcg cttcaagttc ggagctatga tgaaatcggg catgtttctg   6900

actttgttta ttaacactgt tttgaacatc accatagcaa gcagggtact ggagcagaga   6960

ctcactgact ccgcctgtgc ggccttcatc ggcgacgaca acatcgttca cggagtgatc   7020

tccgacaagc tgatggcgga gaggtgcgcg tcgtgggtca acatggaggt gaagatcatt   7080

gacgctgtca tgggcgaaaa acccccatat ttttgtgggg gattcatagt ttttgacagc   7140

gtcacacaga ccgcctgccg tgtttcagac ccacttaagc gcctgttcaa gttgggtaag   7200

ccgctaacag ctgaagacaa gcaggacgaa gacaggcgac gagcactgag tgacgaggtt   7260

agcaagtggt tccggacagg cttgggggcc gaactggagg tggcactaac atctaggtat   7320

gaggtagagg gctgcaaaag tatcctcata gccatggcca ccttggcgag ggacattaag   7380

gcgtttaaga aattgagagg acctgttata cacctctacg gcggtcctag attggtgcgt   7440

taatacacag aattctgatt ggatcccgcc accatgatca agctgaagtt cggggtgttc   7500

ttcaccgtgc tgctgagcag cgcctacgcc cacgggaccc ctcagaacat caccgacctg   7560

tgcgccgagt accacaacac ccagatctac accctgaacg acaagatttt cagctacacc   7620

gaaagcctgg caggaaaaag agagatggcc atcatcacct tcaaaaacgg cgccatcttc   7680

caggtggagg tgcccggcag ccagcacatc gatagccaga agaaggccat cgaaagaatg   7740

aaggacacac tgagaatcgc ctacctgacc gaggccaagg tggaaaagct gtgcgtgtgg   7800

aataataaga ccccccacgc catcgccgcc atcagcatgg ccaaccagta catcaaggca   7860

aacagcaaat tcatcggaat caccgaaaaa gccatgcacg tggcacagcc cgccgtggtg   7920

ctggcaagct ccagaggaat cgcctccttc gtgtgcgagt acgccagccc cggaaaggcc   7980

acagaggtga gagtgaccgt gctgagacag gccgactccc aggtgaccga agtgtgtgct   8040

gccacataca tgatgggcaa cgagctgacc ttcctggacg attccatctg caccggaacc   8100

agcagtggaa accaggtgaa cctgaccatt cagggcctga gggccatgga caccggactg   8160

tacatctgca aggtggagct gatgtacccc ccccctact acctgggcat cggaaacgga   8220

acccagatct atgtgatcga ccccgagcca tgtcccgaca gcgactttac cgtgaccgtg   8280

cccaaggacc tgtacgtggt ggagtacggc tctaacatga ccatcgagtg taaatttccc   8340

gtggagaagc agctggacct ggcagccctg atcgtgtact gggagatgga ggacaagaac   8400

atcatccagt ttgtgcacgg cgaggaagac ctgaaggtgc agcactcctc atacagacag   8460
```

-continued agagccagac tgctgaaaga ccagctgagc ctgggcaacg cagccctgca gatcaccgac 8520
gtgaagctgc aggacgccgg agtgtacaga tgcatgatca gctacggagg ggcagactac 8580
aagagaatca ccgtgaaagt gaacgcaccc tacaacaaaa tcaaccagag aatcctggtg 8640
gtggaccccg tgaccagcga gcacgagctg acctgccagg ccgagggcta ccccaaggca 8700
gaggtgatct ggaccagcag cgaccaccag gtgctgagcg gcaagaccac caccaccaat 8760
agcaaaagag aggaaaagct gttcaacgtg accagcacac tgagaattaa tacaaccacc 8820
aacgagatct tctactgcac attcagaaga ctggaccccg aagaaaacca caccgccgag 8880
ctggtgatcc ccgaactgcc cctggcccac cccccctaacg aaagaaccca cctggtgatc 8940
ctgggcgcca tcctgctgtg cctgggagtg gccctgacct tcatcttccg cctgagaaag 9000
ggcaggatga tggacgtgaa aaagtgcggc atccaggaca caaacagcaa aaagcagagc 9060
gatacccacc tggaggagac cgccaaattt gtggccgcct ggaccctgaa ggcagccgct 9120
tgagaattcg gcccctctcc ctcccccccc cctaacgtta ctggccgaag ccgcttggaa 9180
taaggccggt gtgcgtttgt ctatatgtta ttttccacca tattgccgtc ttttggcaat 9240
gtgagggccc ggaaacctgg ccctgtcttc ttgacgagca ttcctagggg tctttcccct 9300
ctcgccaaag gaatgcaagg tctgttgaat gtcgtgaagg aagcagttcc tctggaagct 9360
tcttgaagac aaacaacgtc tgtagcgacc ctttgcaggc agcggaaccc cccacctggc 9420
gacaggtgcc tctgcggcca aaagccacgt gtataagata cacctgcaaa ggcggcacaa 9480
ccccagtgcc acgttgtgag ttggatagtt gtggaaagag tcaaatggct ctcctcaagc 9540
gtattcaaca aggggctgaa ggatgcccag aaggtacccc attgtatggg atctgatctg 9600
gggcctcggt gcacatgctt tacatgtgtt tagtcgaggt taaaaaaacg tctaggcccc 9660
ccgaaccacg gggacgtggt tttcctttga aaaacacgat gataagcttg ccacaacccg 9720
cgcgcttaat taacccgggg ccaccatgga gcgggtgcag cccctggagg agaacgtggg 9780
caacgccgcc agacccaggt tcgagagaaa caagctgctg ctggtggcca gcgtgatcca 9840
gggactgggc ctgctgctgt gcttcaccta tatttgcctg cactttagtg ccctgcaggt 9900
gagtcataga tacccccgca ttcagtccat caaagtgcag ttcaccgagt ataagaagga 9960
gaagggattc attctgacct cccagaagga ggacgagatc atgaaggtgc agaacaatag 10020
cgtgatcatc aactgtgacg gcttttacct gatttcactg aaaggatact tcagccagga 10080
ggtgaatatc agcctgcact accagaaaga cgaggagccc ctgttccagc tgaagaaggt 10140
gaggagcgtg aacagcctga tggtggccag cctgacctac aaggacaaag tgtacctgaa 10200
cgtgaccacc gacaacacca gcctggatga ttttcacgtg aacggaggcg agctgatcct 10260
gatccatcag aaccccggcg agttctaagg gtaattaatt gacgttttac ggccgccggt 10320
ggcgcccgcg cccggcggcc cgtccctggc cgttgcaggc cactccggtg gctcccgtcg 10380
tccccgactt ccaggcccag cagatgcagc aactcatcag cgccgtaaat gcgctgacaa 10440
tgagacagaa cgcaattgct cctgctaggc ctcccaaacc aaagaagaag aagacaacca 10500
aaccaaagcc gaaaacgcag cccaagaaga tcaacggaaa aacgcagcag caaaagaaga 10560
aagacaagca agccgacaag aagaagaaga aacccggaaa aagagaaaga atgtgcatga 10620
agattgaaaa tgactgtatc ttcgtatgcg gctagccaca gtaacgtagt gtttccagac 10680
atgtcgggca ccgcactatc atgggtgcag aaaatctcgg gtggtctggg ggccttcgca 10740
atcggcgcta tcctggtgct ggttgtggtc acttgcattg ggctccgcag ataagttagg 10800
gtaggcaatg gcattgatat agcaagaaaa ttgaaaacag aaaaagttag ggtaagcaat 10860
ggcatataac cataactgta taacttgtaa caaagcgcaa caagacctgc gcaattggcc 10920
ccgtggtccg cctcacggaa actcggggca actcatattg acacattaat tggcaataat 10980
tggaagctta cataagctta attcgacgaa taattggatt tttattttat tttgcaattg 11040
gtttttaata tttccaaaaa aaaaaaaaaa aaaaaaaaaa aaaaaaaaaa aaaaaaaaaa 11100
aaaaaaaaaa aaactagaga tcataatcag ccatatcaca tctgtagagg ttttacttgc 11160
tttaaaaaac ctcccacacc tccccctgaa cctgaaacat aaaatgaatg caattgttgt 11220
tgttaacttg tttattgcag cttataatgg ttacaaataa agcaatagca tcacaaattt 11280
cacaaataaa gcattttttt cactgcattc tagttgtggt ttgtccaaac tcatcaatgt 11340
atcttatcat gtctggatct agtctgcatt aatgaatcgg ccaacgcgcg gggagaggcg 11400
gtttgcgtat tgggcgctct tccgcttcct cgctcactga ctcgctgcgc tcggtcgttc 11460
ggctgcggcg agcggtatca gctcactcaa aggcggtaat acggttatcc acagaatcag 11520
gggataacgc aggaaagaac atgtgagcaa aaggccagca aaaggccagg aaccgtaaaa 11580
aggccgcgtt gctggcgttt ttccataggc tccgcccccc tgacgagcat cacaaaaatc 11640
gacgctcaag tcagaggtgg cgaaacccga caggactata aagataccag gcgtttcccc 11700
ctggaagctc cctcgtgcgc tctcctgttc cgaccctgcc gcttaccgga tacctgtccg 11760
cctttctccc ttcgggaagc gtggcgcttt ctcatagctc acgctgtagg tatctcagtt 11820
cggtgtaggt cgttcgctcc aagctgggct gtgtgcacga accccccgtt cagcccgacc 11880
gctgcgcctt atccggtaac tatcgtcttg agtccaaccc ggtaagacac gacttatcgc 11940
cactggcagc agccactggt aacaggatta gcagagcgag gtatgtaggc ggtgctacag 12000
agttcttgaa gtggtggcct aactacggct acactagaag aacagtattt ggtatctgcg 12060
ctctgctgaa gccagttacc ttcggaaaaa gagttggtag ctcttgatcc ggcaaacaaa 12120
ccaccgctgg tagcggtggt ttttttgttt gcaagcagca gattacgcgc agaaaaaaag 12180
gatctcaaga agatcctttg atcttttcta cggggtctga cgctcagtgg aacgaaaact 12240
cacgttaagg gattttggtc atgagattat caaaaaggat cttcacctag atccttttaa 12300
attaaaaatg aagttttaaa tcaatctaaa gtatatatga gtaaacttgg tctgacagac 12360
tagtatgatt gaacaagatg gattgcacgc aggttctccg gccgcttggg tggagaggct 12420
attcggctat gactgggcac aacagacaat cggctgctct gatgccgccg tgttccggct 12480
gtcagcgcag gggcgcccgg ttctttttgt caagaccgac ctgtccggtg ccctgaatga 12540
actgcaagac gaggcagcgc ggctatcgtg gctggccacg acgggcgttc cttgcgcagc 12600
tgtgctcgac gttgtcactg aagcgggaag ggactggctg ctattgggcg aagtgccggg 12660
gcaggatctc ctgtcatctc accttgctcc tgccgagaaa gtatccatca tggctgatgc 12720
aatgcggcgg ctgcatacgc ttgatccggc tacctgccca ttcgaccacc aagcgaaaca 12780
tcgcatcgag cgagcacgta ctcggatgga agccggtctt gtcgatcagg atgatctgga 12840
cgaagagcat caggggctcg cgccagccga actgttcgcc aggctcaagg cgagtatgcc 12900
cgacggcgag gatctcgtcg tgacccatgg cgatgcctgc ttgccgaata tcatggtgga 12960
aaatggccgc ttttctggat tcatcgactg tggccggctg ggtgtggcgg accgctatca 13020
ggacatagcg ttggctaccc gtgatattgc tgaagagctt ggcggcgaat gggctgaccg 13080
cttcctcgtg ctttacggta tcgccgctcc cgattcgcag cgcatcgcct tctatcgcct 13140
tcttgacgag ttcttctgac tcgaggcatg caccatgatt acgaattcac gcgtgcatgc 13200
tcgggggacg atcgtcgggg ggctcggggg acgatcgtcg gggggctcgg gggacgatcg 13260
tcggggggct cgggggacga tcgtcggggg gctcgggcat gcacgcgtaa gcttggcact 13320
ggccgaccat gattacgaat tcacgcgtgc atgctcgggg gacgatcgtc ggggggctcg 13380
ggggacgatc gtcggggggc tcgggggacg atcgtcgggg ggctcggggg acgatcgtcg 13440
gggggctcgg gcatgcacgc gtaagcttgg cactggccgg catgcaagct gcaggcatgc 13500
accatgatta cgaattcacg cgtgcatgct cgggggacga tcgtcggggg gctcggggga 13560
cgatcgtcgg ggggctcggg ggacgatcgt cggggggctc gggggacgat cgtcgggggg 13620
ctcgggcatg cacgcgtaag cttggcactg gccgaccatg attacgaatt cacgcgtgca 13680
tgctcggggg acgatcgtcg gggggctcgg gggacgatcg tcggggggct cgggggacga 13740
tcgtcggggg gctcggggga cgatcgtcgg ggggctcggg catgcacgcg taagcttggc 13800
actggccggc atgcaagctc ggatccaccg gtcgccacca tggtgagcaa catgcaagct 13860
cgtaatcaat tacggggtca ttagttcata gcccatatat ggagttccgc gttacataac 13920
ttacggtaaa tggcccgcct ggctgaccgc ccaacgaccc ccgcccattg acgtcaataa 13980
tgacgtatgt tcccatagta acgccaatag ggactttcca ttgacgtcaa tgggtggagt 14040
atttacggta aactgcccac ttggcagtac atcaagtgta tcatatgcca agtacgcccc 14100
ctattgacgt caatgacggt aaatggcccg cctggcatta tgcccagtac atgaccttat 14160
gggactttcc tacttggcag tacatctacg tattagtcat cgctattacc atggtgatgc 14220
ggttttggca gtacatcaat gggcgtggat agcggtttga ctcacgggga tttccaagtc 14280
tccaccccat tgacgtcaat gggagtttgt tttggcacca aaatcaacgg gactttccaa 14340
aatgtcgtaa caactccgcc ccattgacgc aaatgggcgg taggcgtgta cggtgggagg 14400
tctatataag cagagctctc tggctaacta gagaacccac t 14441

<210> SEQ ID NO 2
<211> LENGTH: 372
<212> TYPE: DNA
<213> ORGANISM: Artificial Sequence
<220> FEATURE:
<223> OTHER INFORMATION: Polynucleotide of CTB

<400> SEQUENCE: 2
atgatcaagc tgaagttcgg ggtgttcttc accgtgctgc tgagcagcgc ctacgcccac 60
gggacccctc agaacatcac cgacctgtgc gccgagtacc acaacaccca gatctacacc 120
ctgaacgaca agattttcag ctacaccgaa agcctggcag gaaaaagaga gatggccatc 180
atcaccttca aaaacggcgc catcttccag gtggaggtgc ccggcagcca gcacatcgat 240
agccagaaga aggccatcga aagaatgaag gacacactga gaatcgccta cctgaccgag 300
gccaaggtgg aaaagctgtg cgtgtggaat aataagaccc cccacgccat cgccgccatc 360
agcatggcca ac 372

<210> SEQ ID NO 3
<211> LENGTH: 42
<212> TYPE: DNA
<213> ORGANISM: Artificial Sequence
<220> FEATURE:
<223> OTHER INFORMATION: Polynucleotide of tetanus toxin helper T cell epitopes

<400> SEQUENCE: 3
cagtacatca aggcaaacag caaattcatc ggaatcaccg aa 42

<210> SEQ ID NO 4
<211> LENGTH: 39
<212> TYPE: DNA
<213> ORGANISM: Artificial Sequence
<220> FEATURE:
<223> OTHER INFORMATION: Polynucleotide of pan-DR helper T cell epitopes

<400> SEQUENCE: 4
gccaaatttg tggccgcctg gaccctgaag gcagccgct 39

<210> SEQ ID NO 5
<211> LENGTH: 18
<212> TYPE: DNA
<213> ORGANISM: Artificial Sequence
<220> FEATURE:
<223> OTHER INFORMATION: Polynucleotide of Linker G6

<400> SEQUENCE: 5
ggcggcggcg gcggcggc 18

<210> SEQ ID NO 6
<211> LENGTH: 1413
<212> TYPE: DNA
<213> ORGANISM: Artificial Sequence
<220> FEATURE:
<223> OTHER INFORMATION: Polynucleotide of S antigen RBD- (G4S)2-S2

<400> SEQUENCE: 6
cgcgtgcagc ccaccgagag catcgtgcgc ttccccaaca tcaccaacct gtgccccttc 60
ggcgaggtgt tcaacgccac ccgcttcgcc agcgtgtacg cctggaaccg caagcgcatc 120
agcaactgcg tggccgacta cagcgtgctg tacaacagcg ccagcttcag caccttcaag 180
tgctacggcg tgagccccac caagctgaac gacctgtgct tcaccaacgt gtacgccgac 240
agcttcgtga tccgcggcga cgaggtgcgc cagatcgccc ccggccagac cggcaagatc 300
gccgactaca actacaagct gcccgacgac ttcaccggct gcgtgatcgc ctggaacagc 360
aacaacctgg acagcaaggt gggcggcaac tacaactacc tgtaccgcct gttccgcaag 420
agcaacctga agcccttcga gcgcgacatc agcaccgaga tctaccaggc cggcagcacc 480
ccctgcaacg gcgtggaggg cttcaactgc tacttccccc tgcagagcta cggcttccag 540
cccaccaacg gcgtgggcta ccagccctac cgcgtggtgg tgctgagctt cgagctgctg 600
cacgcccccg ccaccgtgtg cggccccaag aagagcacca acctggtgaa gaacaagtgc 660
gtgaacttcg gcggcggcgg cagcggcggc ggcggcagcg tgctgaacga catcctgagc 720
cgcctggaca aggtggaggc cgaggtgcag atcgaccgcc tgatcaccgg ccgcctgcag 780
agcctgcaga cctacgtgac ccagcagctg atccgcgccg ccgagatccg cgccagcgcc 840
aacctggccg ccaccaagat gagcgagtgc gtgctgggcc agagcaagcg cgtggacttc 900
tgcggcaagg gctaccacct gatgagcttc ccccagagcg ccccccacgg cgtggtgttc 960
ctgcacgtga cctacgtgcc cgcccaggag aagaacttca ccaccgcccc cgccatctgc 1020
cacgacggca aggcccactt cccccgcgag ggcgtgttcg tgagcaacgg cacccactgg 1080
ttcgtgaccc agcgcaactt ctacgagccc cagatcatca ccaccgacaa caccttcgtg 1140
agcggcaact gcgacgtggt gatcggcatc gtgaacaaca ccgtgtacga ccccctgcag 1200
cccgagctgg acagcttcaa ggaggagctg gacaagtact tcaagaacca caccagcccc 1260
gacgtggacc tgggcgacat cagcggcatc aacgccagcg tggtgaacat ccagaaggag 1320

```
atcgaccgcc tgaacgaggt ggccaagaac ctgaacgaga gcctgatcga cctgcaggag   1380

ctgggcaagt acgagcagta catcaagtgg ccc                                1413


<210> SEQ ID NO 7
<211> LENGTH: 96
<212> TYPE: DNA
<213> ORGANISM: Artificial Sequence
<220> FEATURE:
<223> OTHER INFORMATION: Polynucleotide of Foldon-CPPCP

<400> SEQUENCE: 7

ggctacatcc ccgaggcccc ccgcgacggc caggcctacg tgcgcaagga cggcgagtgg     60

gtgctgctga gcaccttcct gtgccccccc tgcccc                               96


<210> SEQ ID NO 8
<211> LENGTH: 84
<212> TYPE: DNA
<213> ORGANISM: Artificial Sequence
<220> FEATURE:
<223> OTHER INFORMATION: Polynucleotide of Furin 2A

<400> SEQUENCE: 8

cgcgccaagc gcgcccccgt gaagcagacc ctgaacttcg acctgctgaa gctggccggc     60

gacgtggaga gcaaccccgg cccc                                            84


<210> SEQ ID NO 9
<211> LENGTH: 51
<212> TYPE: DNA
<213> ORGANISM: Artificial Sequence
<220> FEATURE:
<223> OTHER INFORMATION: Polynucleotide of ERISS

<400> SEQUENCE: 9

atgcgctaca tgatcctggg cctgctggcc ctggccgccg tgtgcagcgc c              51


<210> SEQ ID NO 10
<211> LENGTH: 699
<212> TYPE: DNA
<213> ORGANISM: Artificial Sequence
<220> FEATURE:
<223> OTHER INFORMATION: Polynucleotide of NP

<400> SEQUENCE: 10

gccctgaaca cccccaagga ccacatcggc acccgcaacc ccgccaacaa cgccgccatc     60

gtgctgcagc tgccccaggg caccaccctg cccaagggct tctacgccga gggcagccgc    120

ggcggcagcc aggccagcag ccgcagcagc agccgcagcc gcaacagcag ccgcaacagc    180

acccccggca gcagccgcgg caccagcccc gcccgcatgg ccggcaacgg cggcgacgcc    240

gccctggccc tgctgctgct ggaccgcctg aaccagctgg agagcaagat gagcggcaag    300

ggccagcagc agcagggcca gaccgtgacc aagaagagcg ccgccgaggc cagcaagaag    360

ccccgccaga agcgcaccgc caccaaggcc tacaacgtga cccaggcctt cggccgccgc    420

ggccccgagc agacccaggg caacttcggc gaccaggagc tgatccgcca gggcaccgac    480

tacaagcact ggccccagat cgcccagttc gcccccagcg ccagcgcctt cttcggcatg    540

agccgcatcg gcatggaggt gacccccagc ggcacctggc tgacctacac cggcgccatc    600

aagctggacg acaaggaccc caacttcaag gaccaggtga tcctgctgaa caagcacatc    660

gacgcctaca agaccttccc ccccaccgag cccaagtga                           699
```

<210> SEQ ID NO 11
<211> LENGTH: 569
<212> TYPE: DNA
<213> ORGANISM: Artificial Sequence
<220> FEATURE:
<223> OTHER INFORMATION: Polynucleotide of IRES

<400> SEQUENCE: 11
gcccctctcc ctcccccccc cctaacgtta ctggccgaag ccgcttggaa taaggccggt 60
gtgcgtttgt ctatatgtta ttttccacca tattgccgtc ttttggcaat gtgagggccc 120
ggaaacctgg ccctgtcttc ttgacgagca ttcctagggg tctttcccct ctcgccaaag 180
gaatgcaagg tctgttgaat gtcgtgaagg aagcagttcc tctggaagct tcttgaagac 240
aaacaacgtc tgtagcgacc ctttgcaggc agcggaaccc cccacctggc gacaggtgcc 300
tctgcggcca aaagccacgt gtataagata cacctgcaaa ggcggcacaa ccccagtgcc 360
acgttgtgag ttggatagtt gtggaaagag tcaaatggct ctcctcaagc gtattcaaca 420
aggggctgaa ggatgcccag aaggtacccc attgtatggg atctgatctg gggcctcggt 480
gcacatgctt tacatgtgtt tagtcgaggt taaaaaaacg tctaggcccc ccgaaccacg 540
gggacgtggt tttcctttga aaaacacga 569

<210> SEQ ID NO 12
<211> LENGTH: 543
<212> TYPE: DNA
<213> ORGANISM: Artificial Sequence
<220> FEATURE:
<223> OTHER INFORMATION: Polynucleotide of OX40L

<400> SEQUENCE: 12
atggagcggg tgcagcccct ggaggagaac gtgggcaacg ccgccagacc caggttcgag 60
agaaacaagc tgctgctggt ggccagcgtg atccagggac tgggcctgct gctgtgcttc 120
acctatattt gcctgcactt tagtgccctg caggtgagtc atagataccc ccgcattcag 180
tccatcaaag tgcagttcac cgagtataag aaggagaagg gattcattct gacctcccag 240
aaggaggacg agatcatgaa ggtgcagaac aatagcgtga tcatcaactg tgacggcttt 300
tacctgattt cactgaaagg atacttcagc caggaggtga atatcagcct gcactaccag 360
aaagacgagg agcccctgtt ccagctgaag aaggtgagga gcgtgaacag cctgatggtg 420
gccagcctga cctacaagga caaagtgtac ctgaacgtga ccaccgacaa caccagcctg 480
gatgattttc acgtgaacgg aggcgagctg atcctgatcc atcagaaccc cggcgagttc 540
taa 543

<210> SEQ ID NO 13
<211> LENGTH: 4159
<212> TYPE: DNA
<213> ORGANISM: Artificial Sequence
<220> FEATURE:
<223> OTHER INFORMATION: Polynucleotide of pZDVac-CRSNPO recombinant
plasmid

<400> SEQUENCE: 13
atgatcaagc tgaagttcgg ggtgttcttc accgtgctgc tgagcagcgc ctacgcccac 60
gggacccctc agaacatcac cgacctgtgc gccgagtacc acaacaccca gatctacacc 120
ctgaacgaca agattttcag ctacaccgaa agcctggcag gaaaaagaga gatggccatc 180
atcaccttca aaaacggcgc catcttccag gtggaggtgc ccggcagcca gcacatcgat 240

-continued

```
agccagaaga aggccatcga aagaatgaag gacacactga gaatcgccta cctgaccgag    300
gccaaggtgg aaaagctgtg cgtgtggaat aataagaccc cccacgccat cgccgccatc    360
agcatggcca accagtacat caaggcaaac agcaaattca tcggaatcac cgaagccaaa    420
tttgtggccg cctggaccct gaaggcagcc gctggcggcg gcggcggcgg ccgcgtgcag    480
cccaccgaga gcatcgtgcg cttccccaac atcaccaacc tgtgcccctt cggcgaggtg    540
ttcaacgcca cccgcttcgc cagcgtgtac gcctggaacc gcaagcgcat cagcaactgc    600
gtggccgact acagcgtgct gtacaacagc gccagcttca gcaccttcaa gtgctacggc    660
gtgagcccca ccaagctgaa cgacctgtgc ttcaccaacg tgtacgccga cagcttcgtg    720
atccgcggcg acgaggtgcg ccagatcgcc cccggccaga ccggcaagat cgccgactac    780
aactacaagc tgcccgacga cttcaccggc tgcgtgatcg cctggaacag caacaacctg    840
gacagcaagg tgggcggcaa ctacaactac ctgtaccgcc tgttccgcaa gagcaacctg    900
aagcccttcg agcgcgacat cagcaccgag atctaccagg ccggcagcac cccctgcaac    960
ggcgtggagg gcttcaactg ctacttcccc ctgcagagct acggcttcca gcccaccaac   1020
ggcgtgggct accagcccta ccgcgtggtg gtgctgagct tcgagctgct gcacgccccc   1080
gccaccgtgt gcggccccaa gaagagcacc aacctggtga agaacaagtg cgtgaacttc   1140
ggcggcggcg gcagcggcgg cggcggcagc gtgctgaacg acatcctgag ccgcctggac   1200
aaggtggagg ccgaggtgca gatcgaccgc ctgatcaccg gccgcctgca gagcctgcag   1260
acctacgtga cccagcagct gatccgcgcc gccgagatcc gcgccagcgc caacctggcc   1320
gccaccaaga tgagcgagtg cgtgctgggc cagagcaagc gcgtggactt ctgcggcaag   1380
ggctaccacc tgatgagctt cccccagagc gcccccacg gcgtggtgtt cctgcacgtg   1440
acctacgtgc ccgcccagga gaagaacttc accaccgccc ccgccatctg ccacgacggc   1500
aaggcccact tcccccgcga gggcgtgttc gtgagcaacg gcacccactg gttcgtgacc   1560
cagcgcaact tctacgagcc ccagatcatc accaccgaca acaccttcgt gagcggcaac   1620
tgcgacgtgg tgatcggcat cgtgaacaac accgtgtacg acccccctgca gcccgagctg   1680
gacagcttca aggaggagct ggacaagtac ttcaagaacc acaccagccc cgacgtggac   1740
ctgggcgaca tcagcggcat caacgccagc gtggtgaaca tccagaagga gatcgaccgc   1800
ctgaacgagg tggccaagaa cctgaacgag agcctgatcg acctgcagga gctgggcaag   1860
tacgagcagt acatcaagtg gccctggtac atctggctgg gcttcatcgc cggcctgatc   1920
gccatcgtga tggtgaccat catgctgtgc tgcatgacca gctgctgcag ctgcctgaag   1980
ggctgctgca gctgcggcag ctgctgcaag ttcgacgagg acgacagcga gcccgtgctg   2040
aagggcgtga agctgcacta caccggctac atccccgagg ccccccgcga cggccaggcc   2100
tacgtgcgca aggacggcga gtgggtgctg ctgagcacct tcctgtgccc cccctgcccc   2160
cgcgccaagc gcgcccccgt gaagcagacc ctgaacttcg acctgctgaa gctggccggc   2220
gacgtggaga gcaaccccgg ccccatgcgc tacatgatcc tgggcctgct ggccctggcc   2280
gccgtgtgca gcgccgccct gaacaccccc aaggaccaca tcggcacccg caaccccgcc   2340
aacaacgccg ccatcgtgct gcagctgccc cagggcacca ccctgcccaa gggcttctac   2400
gccgagggca gccgcggcgg cagccaggcc agcagccgca gcagcagccg cagccgcaac   2460
agcagccgca acagcacccc cggcagcagc cgcggcacca gccccgcccg catggccggc   2520
aacggcggcg acgccgccct ggccctgctg ctgctggacc gcctgaacca gctggagagc   2580
aagatgagcg gcaagggcca gcagcagcag ggccagaccg tgaccaagaa gagcgccgcc   2640
```

```
gaggccagca agaagccccg ccagaagcgc accgccacca aggcctacaa cgtgacccag   2700

gccttcggcc gccgcggccc cgagcagacc cagggcaact tcggcgacca ggagctgatc   2760

cgccagggca ccgactacaa gcactggccc cagatcgccc agttcgcccc cagcgccagc   2820

gccttcttcg gcatgagccg catcggcatg gaggtgaccc ccagcggcac ctggctgacc   2880

tacaccggcg ccatcaagct ggacgacaag gaccccaact tcaaggacca ggtgatcctg   2940

ctgaacaagc acatcgacgc ctacaagacc ttccccccca ccgagcccaa gtgagaattc   3000

ggcccctctc cctccccccc ccctaacgtt actggccgaa gccgcttgga ataaggccgg   3060

tgtgcgtttg tctatatgtt attttccacc atattgccgt cttttggcaa tgtgagggcc   3120

cggaaacctg gccctgtctt cttgacgagc attcctaggg gtctttcccc tctcgccaaa   3180

ggaatgcaag gtctgttgaa tgtcgtgaag gaagcagttc ctctggaagc ttcttgaaga   3240

caaacaacgt ctgtagcgac cctttgcagg cagcggaacc ccccacctgg cgacaggtgc   3300

ctctgcggcc aaaagccacg tgtataagat acacctgcaa aggcggcaca accccagtgc   3360

cacgttgtga gttggatagt tgtggaaaga gtcaaatggc tctcctcaag cgtattcaac   3420

aaggggctga aggatgccca gaaggtaccc cattgtatgg gatctgatct ggggcctcgg   3480

tgcacatgct ttacatgtgt ttagtcgagg ttaaaaaaac gtctaggccc cccgaaccac   3540

ggggacgtgg ttttcctttg aaaaacacga tgataagctt gccacaaccc gcgcgcttaa   3600

ttaacccggg gccaccatgg agcgggtgca gcccctggag gagaacgtgg gcaacgccgc   3660

cagacccagg ttcgagagaa acaagctgct gctggtggcc agcgtgatcc agggactggg   3720

cctgctgctg tgcttcacct atatttgcct gcactttagt gccctgcagg tgagtcatag   3780

atacccccgc attcagtcca tcaaagtgca gttcaccgag tataagaagg agaagggatt   3840

cattctgacc tcccagaagg aggacgagat catgaaggtg cagaacaata gcgtgatcat   3900

caactgtgac ggcttttacc tgatttcact gaaaggatac ttcagccagg aggtgaatat   3960

cagcctgcac taccagaaag acgaggagcc cctgttccag ctgaagaagg tgaggagcgt   4020

gaacagcctg atggtggcca gcctgaccta caaggacaaa gtgtacctga acgtgaccac   4080

cgacaacacc agcctggatg attttcacgt gaacggaggc gagctgatcc tgatccatca   4140

gaaccccggc gagttctaa                                                 4159
```

<210> SEQ ID NO 14
<211> LENGTH: 31
<212> TYPE: DNA
<213> ORGANISM: Artificial Sequence
<220> FEATURE:
<223> OTHER INFORMATION: Polynucleotide of Upstream primer F

<400> SEQUENCE: 14

```
cccaggagac ccggttctag agacggacat t                                   31
```

<210> SEQ ID NO 15
<211> LENGTH: 31
<212> TYPE: DNA
<213> ORGANISM: Artificial Sequence
<220> FEATURE:
<223> OTHER INFORMATION: Polynucleotide of Downstream primer R

<400> SEQUENCE: 15

```
aagcggcttc ggccagtaac gttagggggg g                                   31
```

<210> SEQ ID NO 16

```
<211> LENGTH: 5
<212> TYPE: PRT
<213> ORGANISM: Artificial Sequence
<220> FEATURE:
<223> OTHER INFORMATION: Foldon domain

<400> SEQUENCE: 16

Cys Pro Cys Pro Pro
1               5
```

FUSION GENE, RECOMBINANT NOVEL CORONAVIRUS HIGH-EFFICIENCY IMMUNE DNA VACCINE, CONSTRUCTION METHOD AND USE THEREOF

CROSS-REFERENCE TO RELATED APPLICATIONS

This application claims priority to Chinese Patent Application No. 202011310160.8, filed Nov. 20, 2020, the content of which is incorporated by reference in its entirety.

INCORPORATION BY REFERENCE OF SEQUENCE LISTING

The sequence listing in an ASCII text file, named as 41700_SubstituteSequenceListing.txt of 32,399 bytes, created on Dec. 22, 2025, and submitted to the United States Patent and Trademark Office via Patent Center, is incorporated herein by reference.

TECHNICAL FIELD

The present invention relates to the field of biomedical technology, in particular to a fusion gene, a recombinant novel coronavirus high-efficiency immune DNA vaccine (named ZD-nCor19), a construction method and use thereof.

BACKGROUND OF THE INVENTION

Novel coronavirus (COVID-19) is a new strain of coronavirus that has never been found in human body before. The common signs of human infection with novel coronavirus include respiratory symptoms, fever, cough, shortness of breath and dyspnea. In more serious cases, the infection can lead to pneumonia, severe acute respiratory syndrome, renal failure, and even death.

So far, the cumulative number of people infected with novel coronavirus in the world has reached tens of millions, and the cumulative number of deaths has exceeded one million, posing a huge threat to the life, health and safety of all human beings. However, the COVID-19 pandemic is still spreading rapidly in many parts of the world. It has been confirmed that the virus is highly contagious, pathogenic and harmful. There are 7.8 billion people in the world who are at risk of infection, morbidity and death. It is internationally recognized that safe and effective vaccination is an important measure and effective means to protect human safety and health. Therefore, there is an urgent need to develop an effective and safe vaccine that can be used for both prevention and therapy against COVID-19.

At present, there are nearly 200 novel coronavirus vaccines in different stages of development worldwide, of which 10 novel coronavirus vaccines are undergoing phase III clinical trials (as of Oct. 13, 2020), mainly including novel coronavirus inactivated vaccines, recombinant subunit vaccines, adenovirus vector vaccines, attenuated influenza virus vector vaccines, nucleic acid vaccines, etc. Although phased results have been achieved in the research and development of novel coronavirus vaccines, there is still an urgent need for the development of novel coronavirus vaccine varieties that can be used for both prevention and treatment.

SUMMARY

The present invention aims to provide a fusion gene and a recombinant novel coronavirus high-efficiency immune DNA vaccine and a construction method and use thereof.

In the first aspect of the present invention, a fusion gene comprising at least two of the following (1) to (4) is provided:

(1) a gene expressing RBD segment of novel coronavirus COVID-19;

(2) a gene expressing S2 subunit or partial fragment thereof of the novel coronavirus COVID-19;

(3) a gene expressing N protein or partial fragment thereof of the novel coronavirus COVID-19;

(4) a gene expressing fragment selected from the group consisting of CTB, TT, PADRE, Foldon, CPPCP, Furin2A, ERISS, IRES, and OX40L, or combination thereof.

In an embodiment, the fusion gene comprises at least three of the following (1) to (4):

(1) a gene expressing the RBD segment of the novel coronavirus COVID-19;

(2) a gene expressing residues 301-538 in the S2 subunit of the novel coronavirus COVID-19;

(3) a gene expressing residues 138-369 in the N protein of the novel coronavirus COVID-19;

(4) genes expressing the following amino acid fragments: CTB, TT, PADRE, Foldon, CPPCP, Furin2A, ERISS, IRES and OX40L.

In an embodiment, the gene expressing the RBD segment and the gene expressing the residues 301-538 in the S2 subunit are linked to form a fusion fragment; in a preferred embodiment, the nucleotide sequence of the fusion fragment comprises the sequence set forth in SEQ ID NO: 6; the nucleotide sequence of the gene expressing the residues 138-369 in the N protein comprises the sequence set forth in SEQ ID NO:10.

In another embodiment, in the fusion gene:

the nucleotide sequence of the gene expressing the CTB amino acid fragment is set forth in SEQ ID NO: 2;

the nucleotide sequence of the gene expressing the TT amino acid fragment is set forth in SEQ ID NO: 3;

the nucleotide sequence of the gene expressing the PADRE amino acid fragment is set forth in SEQ ID NO: 4;

the gene expressing the Foldon amino acid fragment and the gene expressing the CPPCP amino acid fragment are linked to form a synthetic fragment, and the nucleotide sequence of the synthetic fragment is set forth in SEQ ID NO:7;

the nucleotide sequence of the gene expressing the Furin2A amino acid fragment is set forth in SEQ ID NO: 8;

the nucleotide sequence of the gene expressing the ERISS amino acid fragment is set forth in SEQ ID NO: 9;

the nucleotide sequence of the gene expressing the IRES amino acid fragment is set forth in SEQ ID NO: 11; and/or the nucleotide sequence of the gene expressing the OX40L amino acid fragment is set forth in SEQ ID NO:12.

In one embodiment, in the fusion gene: the gene expressing the RBD segment and the gene expressing the residues 301-538 in the S2 subunit are linked to form a fusion fragment, the upstream of the fusion fragment is sequentially linked with the genes expressing the amino acid fragments of CTB, TT and PADRE, and the downstream of the fusion fragment is sequentially linked with the genes expressing the amino acid fragments of Foldon, CPPCP and Furin2A; and/or the gene expressing the ERISS amino acid fragment is linked upstream of the gene expressing the residues 138-369 in the N protein, and the genes expressing the IRES and OX40L amino acid fragments are sequentially linked downstream of the gene expressing the residues 138-369 in the N protein.

In a preferred embodiment, the gene expressing the RBD segment and the gene expressing the residues 301-538 in the S2 subunit are linked by a gene expressing a $(G4S)_2$ linker, the upstream of the fusion fragment and the gene expressing the PADRE amino acid fragment are linked by a gene expressing a linker G6, wherein the nucleotide sequence of the gene expressing the linker G6 is set forth in SEQ ID NO:5.

In further preferred embodiments, the nucleotide sequence of the fusion gene is set forth in SEQ ID NO:13.

In the second aspect of the present invention, a fusion protein obtained by expressing the fusion gene described above is provided.

In the third aspect of the present invention, a recombinant novel coronavirus high-efficiency immune DNA vaccine, named ZD-nCor19, which comprises the above-mentioned fusion gene and vector, is provided.

In one embodiment, the vector is pZDVac vector.

The fourth aspect of the present invention also provides a method for constructing the above-mentioned recombinant novel coronavirus high-efficiency immune DNA vaccine, comprising the following steps of:

1) synthesizing the fusion gene described above;
2) inserting the fusion gene into a pZDVac vector to obtain the recombinant novel coronavirus high-efficiency immune DNA vaccine.

In the fifth aspect of the present invention, the use of the above-mentioned recombinant novel coronavirus high-efficiency immune DNA vaccine in the preparation of a medicine for preventing and/or treating novel coronavirus infection also belongs to the content of the present invention.

In the recombinant novel coronavirus high-efficiency immune DNA vaccine provided by the present invention, the RBD segment of S1 subunit, segment residues 301-538 in the S2 and segment residues 138-369 in the N protein was fused in frame and expressed as the target antigen. In addition, the fusion gene is further combined with other designs, for example, the upstream and downstream of the target antigen gene are respectively linked with gene expressing immune synergism molecule, and the Furin2A protease cleavage site is set between the genes expressing the target antigen. The above designs allow the recombinant novel coronavirus high-efficiency immune DNA vaccine (recombinant plasmid pZDVac-CRSNPO) constructed and obtained by the present invention can not only effectively avoid the ADE-related problems that may be generated by the full-length S protein and the full-length N protein, but also ensure that the fusion protein expressed by fusion gene can cover more epitopes of the novel coronavirus and achieve more comprehensive protection, compared with using only S1 protein or only RBD or only using S1 protein (RBD) and N protein as target antigens. In the design of the target antigen, the vaccine uses only RBD, residues 301-538 in the S2 subunit and residues 138-369 in the N protein, which have smaller fragments relative to the full-length S protein and N protein, not only beneficial to the construction of vaccines, but also make it easier to enter cells, and have high expression efficiency and high immune effect. In addition, the presence of the Furin2A protease cleavage site allows the extracellular secretion of two antigenic segments (RBD and residues 301-538 in the S2 subunit) derived from the S protein, thereby inducing a better humoral immune response, while the antigenic segment (residues 138-369 in the N protein) derived from the N protein can be expressed intracellularly to induce T cell immune response. Thus, the vaccine constructed and obtained by the present invention can efficiently induce humoral immune response and T cell immune response at the same time, and the two synergistically enhance the immune protection effect of the vaccine.

Compared with the prior art, the present invention has the following beneficial effects:

1) High safety: the vaccine of the present invention belongs to the RNA vaccine in the form of DNA, and is not integrated into the chromosome, so it will not cause malignant transformation of cells. Moreover, after the vaccine enters cells, RNA transcription may be carried out on a large scale, resulting in rapid apoptosis of cells, further avoiding the possibility of malignant transformation. In addition, the vaccine is a naked plasmid product, without additional liposomes, aluminum adjuvants, etc., and basically does not cause additional non-specific inflammatory responses. Therefore, in terms of safety, it is the most advantageous and most guaranteed among all types of vaccines.
2) High-efficiency immunity: the vaccine of the present invention belongs to a class of high-efficiency immune DNA vaccines ((ipDNA vaccine) ZD-nCor19) which combines the dual advantages of DNA vaccines and RNA vaccines. The verified results show that by using vaccination via intradermal injection+electrical pulse assisted introduction (two injections, 28 days apart, 1-4 weeks apart in emergencies), the vaccines may efficiently induce mucosal-like surface immune protective efficacy, and induce systemic high-efficiency cellular immune responses, which can not only form a strong superficial immune protection effect, but also have a strong deep protective effect. This kind of immune response belongs to the high-level immune response, which has the characteristics of 'rapid immune decision mobilization', 'group army annihilation campaign' and 'active defense clearance in depth', providing efficient and lasting immune protection for the human body. Once attacked by the virus, systemic immune mobilization can be carried out quickly and efficiently, including the immune response at the superficial mucosal level, as well as systemic innate immunity, humoral immunity and cellular immunity, to quickly kill and clear the novel coronavirus invading the body, prevent the virus from causing disease and increasing serious disease condition, protect life, avoid various sequelae, and complete the efficient killing and clearance of viruses while the body does not produce symptoms or only produces mild symptoms, thus quickly restore health.

In addition, the high-efficiency immunity of the vaccine is also reflected in the ability to enhance the systemic immunity in human bodies. For the elderly with weak immunity and people with serious underlying diseases, the vaccine is an excellent life-protecting vaccine, helping to protect the life and health of the elderly and immune-vulnerable groups.

3) Long-acting immunity and anti-variants: in addition to the high-efficiency immune protection feature of the vaccine of the present invention, the antigen-specific cellular immunity induced by the vaccine will retain the ability of immune memory for years, so the vaccine is also a vaccine that can provide long-acting immune protection. Moreover, in the vaccine design, a partial fragment of the internal N protein of the virus is used as the target antigen, which is extremely stable and rarely produces confirmed mutation, thus the vaccine of the present invention is also a vaccine that can effectively resist virus mutation. Even after some vaccines lose their immune protection efficacy due to the significant variation of virus surface antigens, the vaccine of the present invention can still provide high-efficiency immune protection.

4) Used for both prevention and therapy: the vaccine of the present invention can not only be used as a preventive vaccine, but also can be used for emergency immunotherapy for people who test positive for the virus. The vaccine can induce a high-efficiency cellular immune response quickly, clean the virus in the body in a timely and efficient manner, prevent the condition from getting worse, help save lives, and reduce the fatality rate of the virus. Therefore, the vaccine of the present invention will be a vaccine that can truly protect and save lives.

5) Large manufacturing capacity and low cost: the vaccine of the present invention can use the *E. coli* prokaryotic system for biological fermentation production, so the existing biological fermentation industrial system can be used to establish a new industrial system, so the production of the vaccine can form a huge manufacturing capacity, and the cost is relatively lower. Therefore, it is expected to meet domestic and international demand for this vaccine variety.

6) Highly stability: DNA vaccines generally have strong stability and can be stored and transported at room temperature, while RNA vaccines, protein subunit vaccines and viral vector vaccines, as well as inactivated vaccines require cold chain transportation, which is a particular advantage of DNA vaccines over other types of vaccine varieties. The vaccine provided is a DNA vaccine, thus it has a very great advantage in stability, and can become an excellent choice among the national novel coronavirus vaccine foreign-aid varieties.

7) Broad market: At present, there is no novel coronavirus vaccine on the market against Novel coronavirus, therefore, the effect of the current clinical or under development vaccines cannot be judged. It is necessary to use a variety of vaccines under development to make a "combined boxing" to form a vaccine complementation. The vaccine herein can not only be used alone to provide high-efficiency protection against Novel coronavirus, for other types of vaccines, it can also be used for booster immunization, to provide enhanced immune protection in conjunction with other types of vaccines. Furthermore, the vaccine provided herein can even help some vaccines that may have potential ADE effect (antibody-dependent enhancement) overcome the possible ADE effect, and avoid the serious problem of ADE effect aggravating the disease.

In conclusion, the vaccine (ipDNA vaccine) ZD-nCor19 provided herein is expected to have the characteristics and advantages of safety, high efficiency, long-acting, anti-mutation, highly stability and huge manufacturing capacity. It is a DNA vaccine with efficient immune effect, and can be used for routine prevention in population, specific immune protection of immune vulnerable groups such as the elderly, immune enhancement of specific groups, emergency vaccination after virus exposure, coordinated immune enhancement of different types of vaccines, and as a national foreign aid vaccine. As an excellent vaccine for both prevention and therapy, the vaccine is expected to be further developed and utilized.

DETAILED DESCRIPTION OF THE INVENTION

Figure 1:
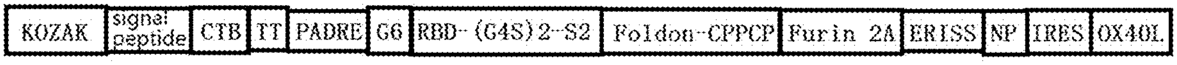
FIG. 1 is a schematic diagram showing the connection structure of target antigens and immune synergism molecules in a recombinant novel coronavirus high-efficiency immune DNA vaccine provided by an example of the present invention.

The present invention aims to provide a recombinant novel coronavirus high-efficiency immune DNA vaccine (ipDNA vaccine) ZD-nCor19 having both preventive and therapeutic functions, as well as construction method and use thereof, which are mainly realized based on the following technical means.

An alphavirus replicase-based DNA (replicon) vector pZDVac is used in the construction of the recombinant novel coronavirus high-efficiency immune DNA vaccine. The pZDVac vector is obtained from the existing pSFV1 plasmid through the following modifications: replacing the original SP6 promoter with the human cytomegalovirus CMV promoter, adding a polyadenylic acid tail SV40 poly (A), and replacing the resistance gene of the pSFV1 plasmid with a kanamycin resistance gene with clinically better safety, and the replicon after the above successful modifications is finally expressed in eukaryotes, and the resulted vector is named pZDVac vector (namely pSVK1 disclosed in the patent document CN105343874A). By using the vector, tedious processes of preparing RNA in vitro is avoided. The vector can be directly transfected into human and animal cells in the form of DNA plasmids, achieving high-level expression of foreign proteins. The vector inherits a function that alphavirus vectors can induce the production of type I IFN to provide adjuvant effect for the expressed antigen, and which has the effect of enhancing immunogenicity.

The following factors in antigen design are fully considered, and optimized design schemes are proposed:

(1) at present, there is still little basic research on the novel coronavirus, and no novel coronavirus vaccine on the market against Novel coronavirus, therefore, there is no exact standard for the selection of the target antigen for the novel coronavirus vaccine, that is, there is no basis to determine which segment of the novel coronavirus antigen is more effective as the vaccine target antigen. Therefore, researchers generally select novel coronavirus antigens based on the development of SARS virus vaccine, and in target antigens selection, researchers generally use the full-length spike glycoprotein (Spike Protein, S protein, which consists of two subunits, S1 and S2) or truncated S protein (S1 subunit and its receptor binding region RBD) form, and the highly conserved nucleocapsid protein N (SARS-CoV-2 nucleocapsid) in the novel coronavirus. It is commonly believed that it is safer to choose the full-length S protein, which contains most of the antigenic epitopes and has a wider coverage; RBD is chosen because it contains a critical neutralizing domain (CND), which can induce potent neutralizing antibody response and possible cross-protection against mutant strains; N protein is chosen because it is a highly immunogenic and conserved phosphoprotein among coronaviruses, which can not only induce specific antibodies, but also specific cytotoxic cell activity, and it is highly conservative among various coronaviruses, so it is relatively less likely to mutate, which can avoid the risk of vaccine failure due to virus mutation (S protein is an antigen that is more likely to mutate in the virus, and if the virus mutates, it is likely to affect the immune efficacy of the vaccine.). Among them, according to the structure of the novel coronavirus and the mechanism of infecting patients, it is generally believed that the S1 subunit and N protein of the novel coronavirus are the main viral antigens that trigger strong immune responses, and are the best viral antigens for vaccine development.

(2) The inventors have considered that the full-length S protein and full-length N protein of the novel coronavirus may cause ADE-associated problems. Therefore, the inventors optimized the design and finally determined that the RBD of the S1 subunit of the S protein, residues 301-538 in the S2 subunit and residues 138-369 in the N protein was chosen for target antigen design. Among them, the RBD of the S1 subunit contains the key neutralizing region, which is the key to vaccine development; residues 301-538 in the S2 subunit contains most of the T cell epitopes, and residues 138-369 in the N protein also contains multiple T cell antigen epitopes. Such a target antigen design can not only effectively avoid the ADE-related problems that may be caused by the full-length S protein and the full-length N protein, but also ensure that the designed fusion protein covers more antigen epitopes, achieving more comprehensive protection, relative to those using S1 protein only or those using RBD only or those using the fusion protein of S1 protein (or RBD) and N protein. At the same time, in the design of the target antigen of the present invention, the RBD, residues 301-538 in the S2 subunit and residues 138-369 in the N protein, which have smaller fragments relative to the full-length S protein and N protein, are used. This design of the target antigen is not only conducive to the construction of vaccines, but also makes it easier to enter into cells, and has high expression efficiency and high immune effect. In addition, in the target antigen design, two antigen segments (RBD and residues 301-538 in the S2 subunit) derived from the S protein are designed for secretory expression, which could induce better humoral immune responses; an antigenic segment (residues 138-369 in the N protein) derived from N protein is designed to be expressed intracellularly, which can further enhance the induced T cell immune response, thus the vaccine constructed based on this design can efficiently induce humoral immune response and T cell immune response simultaneously, and the two synergistically enhance the immune protection effect of the vaccine.

(3) The inventors have also considered that the immunogenicity of the DNA vaccine or viral vector vaccine using antigens alone might be insufficient. Therefore, in order to further improve the immunogenicity of the recombinant novel coronavirus DNA vaccine obtained by construction, and thereby improve its immune protection efficacy, immune synergism molecules suitable for the target antigen in the vaccine constructed by the present invention were also screened and determined, including:

(i) cholera toxin B subunit (CTB): it can initiate innate immunity, activate DC, enhance immune response, help transfer antigens into cells, induce TH1 and TH2 immune pathways, and act as mucosal immune adjuvant;

(ii) tetanus toxin helper T cell epitopes (TT) and pan-DR helper T cell epitopes (PARDE): they can enhance CD4+ T cell responses;

(iii) Foldon-CPPCP: Foldon is a domain that enables non-covalent oligomerization of target proteins. It is derived from the C-terminus of T4 bacteriophage fibrin and consists of 27 amino acids. The oligomerization structure formed by non-covalent force has high stability. The structure will depolymerize when the temperature is higher than 75° C. or in more than 2% SDS at room temperature, and after depolymerization, it can still re-form trimers in a suitable environment. CPPCP (cysteine-proline-proline-cysteine-proline) (SEQ ID NO:16) is similar to antibody hinge region, suitable for bispecific antibodies and fusion proteins, and is easy to granulate the trimeric proteins. This type of immune potentiating molecule can make the antigen expressed by the vaccine form multimers and granules, which can further enhance its immunogenicity;

(iv) ERISS sequence: it is the adenovirus E3 leader sequence, which is an endoplasmic reticulum insertion signal sequence, namely ER insertion signal sequence (ERISS), which can bind to the endoplasmic reticulum signal recognition particle (SRP). Through the characteristic that SRP can bind to the SRP receptor on the surface of the ER membrane, the fusion target antigen can be effectively transported into the ER, and the processing of the antigen by APC and the presentation of MHC class I molecules are enhanced, thereby enhancing the induction of effective protective CTL production;

(v) OX40L: it can provide costimulatory signals for T cell activation.

A series of fusion genes can be obtained by integrating part or all of the genes expressing these immunopotentiating molecules into any one of the genes expressing the RBD, residues 301-538 in the S2 subunit and residues 138-369 in the N protein or a combination thereof. These fusion genes are inserted into the determined pZDVac vector to construct and obtain the recombinant novel coronavirus DNA vaccine of the present invention.

Fusion genes include various combinations (the following description is based on the protein structure after fusion gene expression), such as:

Combination 1: RBD protein and residues 301-538 in the S2 subunit are linked together through $(G4S)_2$ linker, and then cholera toxin B subunit, tetanus toxin helper T cell epitopes (TT) and pan-DR helper T cell epitopes(wherein the pan-DR helper T cell epitopes and RBD proteins are linked by G6 flexible linker) are sequentially linked to the amino terminus (N terminus) of RBD protein. Surprisingly, relative to other linking sequences (for example, tetanus toxin helper T-cell epitope, pan-DR helper T-cell epitope, and cholera toxin B subunit, or tetanus toxin helper T-cell epitope, cholera toxin B subunit and pan-DR helper T cell epitope, etc.), the linking sequence of the three immunepotentiating molecules mentioned above is more conducive to display the target antigen and enhance the immune response induced by the target antigen. Combination 2: Foldon-CPPCP is linked to the carboxy-terminus (C-terminus) of residues 301-538 in the S2 subunit. The function of Foldon is to easily trimerize the antigens, and CPPCP is to further granulate the trimeric antigens. The combination of Foldon and CPPCP makes it easier to multimerize and granulate the target antigen after it is expressed. Compared with soluble antigens, it is easier to be phagocytosed by APC, and can activate Th cells, CTL cells and B cells at the same time, which can stimulate both cellular immunity and humoral immunity, so it can generate a comprehensive immune response and greatly enhance the immune protection effect of the vaccine. In this combination, the inventors unexpectedly find that in relative to other linking sequences (e.g. CPPCP-Foldon) and other positions, combining the two adjuvant molecules, Foldon and CPPCP, and placing them after the fusion fragment of RBD protein and residues 301-538 in the S2 subunit in the linking sequence of Foldon-CPPCP are more conducive to the display of Foldon and CPPCP after expression. If the adjuvant molecules Foldon-CPPCP are placed in other positions of the fusion fragment, it is likely to cause the two adjuvant molecules to be easily encapsulated in the middle of the antigen protein due to their small molecular weight after expression. Thus, the spatial structure of the two adjuvant molecules will not be displayed, and they will not play the role of polymerizing and granulating the target antigen after expression. Combination of Combination 2 and Combination 1 can produce a stacking effect or a synergistic effect.

Combination 3: at the carboxy terminus of CPPCP based on Combination 2 or at the carboxy terminus of residues 301-538 in the S2 subunit based on Combination 1, Furin2A, ERISS and residues 138-369 in the N protein are sequentially linked. Among them, ERISS can enhance the processing of antigens by APC and the presentation by MHC class I molecules, thereby enhancing the T cell immune response of the N protein segment expressed in cells. Furin2A is a protease cleavage site, which can make residues 138-369 in the N protein independently expressed intracellularly to induce a T cell immune response.

Combination 4: based on combination 3, an internal ribosome entry site (IRES) sequence is linked to the C-terminus of residues 138-369 in the N protein, and downstream of the IRES sequence, an OX40L molecule is further linked, which can deliver a second signal for T cell activation, further stimulate the immune response, and induce the immune response to shift to Th1 type high-level immune response.

In addition, a Kozak sequence and a signal peptide sequence (which can also be added to the backbone vector in advance) can be sequentially introduced upstream of the fusion genes in each combination above-mentioned, and the signal peptide can be selected from signal peptides suitable for eukaryotic expression.

FIG. 1 shows an example of the connection structure of the target antigens and immune potentiating molecules in the recombinant novel coronavirus high-efficiency immune DNA vaccine, including the fusion gene integrating the above Combination 1-Combination 4 and the Kozak sequence and signal peptide sequence upstream of the fusion gene.

The design of the structure of the recombinant novel coronavirus DNA vaccine provided by a preferred embodiment of the present invention can generate synergy among the target antigens, among the immunopotentiating molecules, and between the target antigens and the immunopotentiating molecules, so as to improve the immune protection effect of the DNA vaccine. At the same time, the DNA vaccine is designed to express the segments (the RBD and residues 301-538 in the S2 subunit) of S protein and the segment (residues 138-369) of N protein, respectively, in which the S protein segment is the extracellular expression form, and the N protein segment is the intracellular expression form, therefore, they can induce good humoral immune response and T cell immune response at the same time, and can further improve the immune protection effect of the DNA vaccine.

The content of the present invention will be described in detail below with reference to specific examples and accompanying drawings.

In the following, certain exemplary examples are briefly described. As those skilled in the art would realize, the described examples may be modified in various different ways, all without departing from the spirit or scope of the present invention. Accordingly, the drawings and descriptions are to be regarded as illustrative in nature and non-limiting.

The methods used in the following examples are conventional methods unless otherwise specified, and the specific steps can be found in: "Molecular Cloning: A Laboratory Manual" Sambrook, J., Russell, David W., Molecular Cloning: A Laboratory Manual, 3rd edition, 2001, NY, Cold Spring Harbor.

The ways of obtaining various biological materials described in the examples are only to provide a way to obtain experimentally to achieve the purpose of specific disclosure, and should not be a limitation on the source of the biological materials of the present invention. In fact, the sources of the used biological materials are extensive, and any biological materials that can be obtained without violating laws and ethics can be replaced and used according to the teachings in the examples.

All primers and sequences mentioned in the present invention were synthesized using prior art.

EXAMPLE 1

Construction of Recombinant Novel Coronavirus High-Efficiency Immune DNA Vaccine ZD-nCor19

In this example, the pZDVac vector was used as the carrier of the DNA vaccine, the RBD, segment (residues 301-538) in the S2 subunit and segment (residues 138-369) in the N protein of the novel coronavirus were used as the target antigens, and cholera toxin B, tetanus toxin helper T cell epitopes, pan-DR helper T cell epitopes, Foldon-CPPCP, Furin2A, ERISS, IRES and OX40L (the respective corresponding nucleotide sequences are shown in Table 1 below, wherein the RBD and segment (residues 301-538) in the S2 subunit was linked by $(G4S)_2$ (RBD-$(G4S)_2$-S2), Linker G6 in Table 1 is indicated as the linker sequence between RBD and PARDE, the nucleotide sequence of segment (residues 138-369) in the N protein is given as NP in Table 1) were also used as immune synergism molecules to construct a recombinant novel coronavirus high-efficiency immune DNA vaccine. The construction method specifically includes the following steps.

1.1. Preparation and Identification of Expression Vector Backbone

Figure 2:
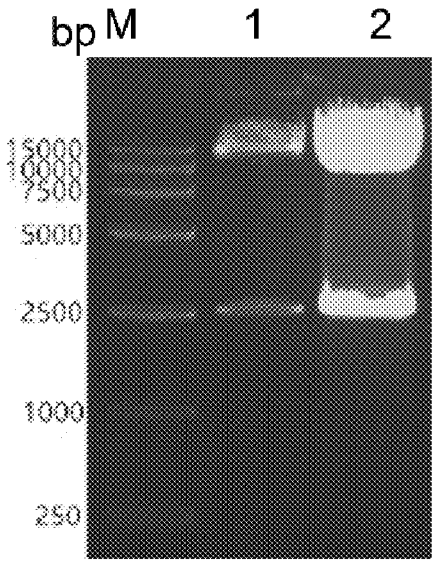
FIG. 2 is a gel electrophoresis photograph of double digested pZDVac-CCCPO plasmid.
Figure 4:
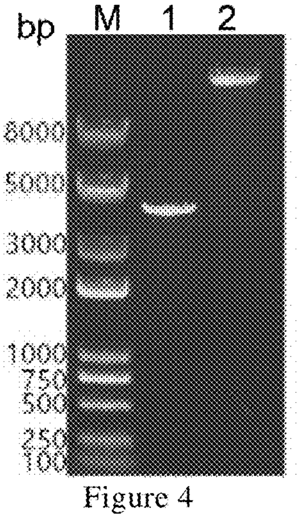
FIG. 4 is a gel electrophoresis photograph showing the recovery and identification of the target gene fragment and vector backbone of the recombinant plasmid pZDVac-CRSNPO.

The pZDVac-CCCPO plasmid (which was obtained by cloning the synthetic gene CTB-TT-CTLA-4+PD-L1 extracellular region-PADRE-IRES-OX40L into a pZDVac vector, and its structure was pZDVac-CTB-TT-CTLA-4+PD-L1 extracellular region-PADRE-IRES-OX40L, the corresponding nucleotide sequence is set forth in SEQ ID NO: 1) was digested by AclI and XbaI restriction enzymes, and the photo of 0.45% gel electrophoresis was shown in FIG. 2, wherein Lanes 1 and 2 were the results of the pZDVac-CCCPO plasmid after double digestion with AclI and XbaI. The recovered large fragment of about 12 kb was pZDVac-IRES-OX40L. The result of re-gel electrophoresis identification of the recovered fragment was shown in Lane 2 in FIG. 4, and it could be used as an expression vector backbone for constructing a novel coronavirus high-efficiency immune DNA vaccine.

1.2. Synthesis and Identification of Gene Fragments

As shown in FIG. 1, gene synthesis was carried out according to the sequence of gene connection of CTB-TT-PARDE-G6-RBD-$(G4S)_2$-S2-Foldon-CPPCP-Furin2A-ERISS-NP (named as first target gene, CRSNP for short), and the restriction sites XbaI, NruI, PmeI were introduced upstream of the first target gene, and a single restriction site AclI was introduced downstream of the first target gene, thus a recombinant plasmid (named pUC57-CRSNP recombinant plasmid) carrying the target gene fragment CRSNP was obtained. The steps were performed by Beijing Biomed Gene Co., Ltd.

Figure 3:
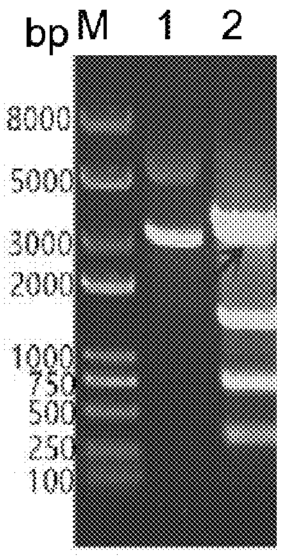
FIG. 3 is a gel electrophoresis photograph of double digested pUC57-CRSNP plasmid.

The pUC57-CRSNP recombinant plasmid was digested by AclI and XbaI restriction enzymes (purchased from New England Biolabs (NEB) Inc.), and the photo of 0.45% agarose gel electrophoresis (Regular Agarose G-10, from Biowest company) was shown in FIG. 3, wherein Lane 1 showed the electrophoresis results of the pUC57-CRSNP recombinant plasmid, and Lane 2 showed the electrophoresis results of the pUC57-CRSNP recombinant plasmid after double digestion with AclI and XbaI. The target gene fragment CRSNP (as shown by the arrow in FIG. 3, named as first target gene fragment)was obtained by recovering (Agarose Gel DNA Recovery Kit (Spin-Columns) from TIANGEN) the target fragment of 3.6 kb. The result of re-gel electrophoresis identification of the recovered first target gene fragment was shown in Lane 1 in FIG. 4. In this example, the inventors also synthesized two other target gene fragments: RBD-$(G4S)_2$-S2-NP (named as second target gene fragment, which differs from the first target gene fragment only in that it was not linked to immune synergism molecules) and Foldon-CPPCP-TT-PARDE-G6-RBD-$(G4S)_2$-S2-CTB-Furin2A-ERISS-NP (named third target gene fragment, which differs from the first target gene fragment in the positions of the immune adjuvant molecules, Foldon-CPPCP and CTB).

TABLE 1

Nucleotide sequence information of each structure in the recombinant novel coronavirus high-efficiency immune DNA vaccine

| Name | Nucleotide sequences |
|---|---|
| cholera toxinB (CTB) | ATGATCAAGCTGAAGTTCGGGGTGTTCTTCACCGTGCTGCT GAGCAGCGCCTACGCCCACGGGACCCCTCAGAACATCACC GACCTGTGCGCCGAGTACCACAACACCCAGATCTACACCCT GAACGACAAGATTTTCAGCTACACCGAAAGCCTGGCAGGA AAAAGAGAGATGGCCATCATCACCTTCAAAAACGGCGCCA TCTTCCAGGTGGAGGTGCCCGGCAGCCAGCACATCGATAG CCAGAAGAAGGCCATCGAAAGAATGAAGGACACACTGAG AATCGCCTACCTGACCGAGGCCAAGGTGGAAAAGCTGTGC GTGTGGAATAATAAGACCCCCCACGCCATCGCCGCCATCA GCATGGCCAAC (SEQ ID NO: 2) |
| tetanus toxin helper T cell epitopes (TT) | CAGTACATCAAGGCAAACAGCAAATTCATCGGAATCACCG AA (SEQ ID NO: 3) |
| pan-DR helper T cell epitopes (PARDE) | GCCAAATTTGTGGCCGCCTGGACCCTGAAGGCAGCCGCT (SEQ ID NO: 4) |
| Linker G6 | GGCGGCGGCGGCGGCGGC (SEQ ID NO: 5) |
| S antigen RBD-$(G4S)_2$-S2 | CGCGTGCAGCCCACCGAGAGCATCGTGCGCTTCCCCAACAT CACCAACCTGTGCCCCTTCGGCGAGGTGTTCAACGCCACCC GCTTCGCCAGCGTGTACGCCTGGAACCGCAAGCGCATCAG |

TABLE 1-continued

Nucleotide sequence information of each structure in the recombinant novel coronavirus high-efficiency immune DNA vaccine

| Name | Nucleotide sequences |
|---|---|
| | CAACTGCGTGGCCGACTACAGCGTGCTGTACAACAGCGCC AGCTTCAGCACCTTCAAGTGCTACGGCGTGAGCCCCACCAA GCTGAACGACCTGTGCTTCACCAACGTGTACGCCGACAGCT TCGTGATCCGCGGCGACGAGGTGCGCCAGATCGCCCCCGG CCAGACCGGCAAGATCGCCGACTACAACTACAAGCTGCCC GACGACTTCACCGGCTGCGTGATCGCCTGGAACAGCAACA ACCTGGACAGCAAGGTGGGCGGCAACTACAACTACCTGTA CCGCCTGTTCCGCAAGAGCAACCTGAAGCCCTTCGAGCGC GACATCAGCACCGAGATCTACCAGGCCGGCAGCACCCCCT GCAACGGCGTGGAGGGCTTCAACTGCTACTTCCCCCTGCAG AGCTACGGCTTCCAGCCCACCAACGGCGTGGGCTACCAGC CCTACCGCGTGGTGGTGCTGAGCTTCGAGCTGCTGCACGCC CCCGCCACCGTGTGCGGCCCCAAGAAGAGCACCAACCTGG TGAAGAACAAGTGCGTGAACTTCGGCGGCGGCGGCAGCGG CGGCGGCGGCAGCGTGCTGAACGACATCCTGAGCCGCCTG GACAAGGTGGAGGCCGAGGTGCAGATCGACCGCCTGATCA CCGGCCGCCTGCAGAGCCTGCAGACCTACGTGACCCAGCA GCTGATCCGCGCCGCCGAGATCCGCGCCAGCGCCAACCTG GCCGCCACCAAGATGAGCGAGTGCGTGCTGGGCCAGAGCA AGCGCGTGGACTTCTGCGGCAAGGGCTACCACCTGATGAG CTTCCCCCAGAGCGCCCCCCACGGCGTGGTGTTCCTGCACG TGACCTACGTGCCCGCCCAGGAGAAGAACTTCACCACCGC CCCCGCCATCTGCCACGACGGCAAGGCCCACTTCCCCCGCG AGGGCGTGTTCGTGAGCAACGGCACCCACTGGTTCGTGAC CCAGCGCAACTTCTACGAGCCCCAGATCATCACCACCGAC AACACCTTCGTGAGCGGCAACTGCGACGTGGTGATCGGCA TCGTGAACAACACCGTGTACGACCCCCTGCAGCCCGAGCT GGACAGCTTCAAGGAGGAGCTGGACAAGTACTTCAAGAAC CACACCAGCCCCGACGTGGACCTGGGCGACATCAGCGGCA TCAACGCCAGCGTGGTGAACATCCAGAAGGAGATCGACCG CCTGAACGAGGTGGCCAAGAACCTGAACGAGAGCCTGATC GACCTGCAGGAGCTGGGCAAGTACGAGCAGTACATCAAGT GGCCC (SEQ ID NO: 6) |
| Foldon-CPPCP | GGCTACATCCCCGAGGCCCCCCGCGACGGCCAGGCCTACG TGCGCAAGGACGGCGAGTGGGTGCTGCTGAGCACCTTCCT GTGCCCCCCCTGCCCC (SEQ ID NO: 7) |
| Furin 2A | CGCGCCAAGCGCGCCCCCGTGAAGCAGACCCTGAACTTCG ACCTGCTGAAGCTGGCCGGCGACGTGGAGAGCAACCCCGG CCCC (SEQ ID NO: 8) |
| ERISS | ATGCGCTACATGATCCTGGGCCTGCTGGCCCTGGCCGCCGT GTGCAGCGCC (SEQ ID NO: 9) |
| NP | GCCCTGAACACCCCCAAGGACCACATCGGCACCCGCAACC CCGCCAACAACGCCGCCATCGTGCTGCAGCTGCCCCAGGG CACCACCCTGCCCAAGGGCTTCTACGCCGAGGGCAGCCGC GGCGGCAGCCAGGCCAGCAGCCGCAGCAGCAGCCGCAGCC GCAACAGCAGCCGCAACAGCACCCCCGGCAGCAGCCGCGG CACCAGCCCCGCCCGCATGGCCGGCAACGGCGGCGACGCC GCCCTGGCCCTGCTGCTGCTGGACCGCCTGAACCAGCTGGA GAGCAAGATGAGCGGCAAGGGCCAGCAGCAGCAGGGCCA GACCGTGACCAAGAAGAGCGCCGCCGAGGCCAGCAAGAA GCCCCGCCAGAAGCGCACCGCCACCAAGGCCTACAACGTG ACCCAGGCCTTCGGCCGCCGCGGCCCCGAGCAGACCCAGG GCAACTTCGGCGACCAGGAGCTGATCCGCCAGGGCACCGA CTACAAGCACTGGCCCCAGATCGCCCAGTTCGCCCCCAGCG CCAGCGCCTTCTTCGGCATGAGCCGCATCGGCATGGAGGTG ACCCCCAGCGGCACCTGGCTGACCTACACCGGCGCCATCA AGCTGGACGACAAGGACCCCAACTTCAAGGACCAGGTGAT CCTGCTGAACAAGCACATCGACGCCTACAAGACCTTCCCCC CCACCGAGCCCAAGTGA (SEQ ID NO: 10) |
| IRES | GCCCCTCTCCCTCCCCCCCCCCTAACGTTACTGGCCGAAGC CGCTTGGAATAAGGCCGGTGTGCGTTTGTCTATATGTTATT TTCCACCATATTGCCGTCTTTTGGCAATGTGAGGGCCCGGA AACCTGGCCCTGTCTTCTTGACGAGCATTCCTAGGGGTCTT TCCCCTCTCGCCAAAGGAATGCAAGGTCTGTTGAATGTCGT GAAGGAAGCAGTTCCTCTGGAAGCTTCTTGAAGACAAACA ACGTCTGTAGCGACCCTTTGCAGGCAGCGGAACCCCCCACC TGGCGACAGGTGCCTCTGCGGCCAAAAGCCACGTGTATAA GATACACCTGCAAAGGCGGCACAACCCCAGTGCCACGTTG TGAGTTGGATAGTTGTGGAAAGAGTCAAATGGCTCTCCTCA AGCGTATTCAACAAGGGGCTGAAGGATGCCCAGAAGGTAC |

TABLE 1-continued

| Nucleotide sequence information of each structure in the recombinant novel coronavirus high-efficiency immune DNA vaccine | |
|---|---|
| Name | Nucleotide sequences |
| | CCCATTGTATGGGATCTGATCTGGGGCCTCGGTGCACATGC TTTACATGTGTTTAGTCGAGGTTAAAAAAACGTCTAGGCCC CCCGAACCACGGGGACGTGGTTTTCCTTTGAAAAACACGA (SEQ ID NO: 11) |
| OX40L | ATGGAGCGGGTGCAGCCCCTGGAGGAGAACGTGGGCAACG CCGCCAGACCCAGGTTCGAGAGAAACAAGCTGCTGCTGGT GGCCAGCGTGATCCAGGGACTGGGCCTGCTGCTGTGCTTCA CCTATATTTGCCTGCACTTTAGTGCCCTGCAGGTGAGTCAT AGATACCCCCGCATTCAGTCCATCAAAGTGCAGTTCACCGA GTATAAGAAGGAGAAGGGATTCATTCTGACCTCCCAGAAG GAGGACGAGATCATGAAGGTGCAGAACAATAGCGTGATCA TCAACTGTGACGGCTTTTACCTGATTTCACTGAAAGGATAC TTCAGCCAGGAGGTGAATATCAGCCTGCACTACCAGAAAG ACGAGGAGCCCCTGTTCCAGCTGAAGAAGGTGAGGAGCGT GAACAGCCTGATGGTGGCCAGCCTGACCTACAAGGACAAA GTGTACCTGAACGTGACCACCGACAACACCAGCCTGGATG ATTTTCACGTGAACGGAGGCGAGCTGATCCTGATCCATCAG AACCCCGGCGAGTTCTAA (SEQ ID NO: 12) |

Figure 5:
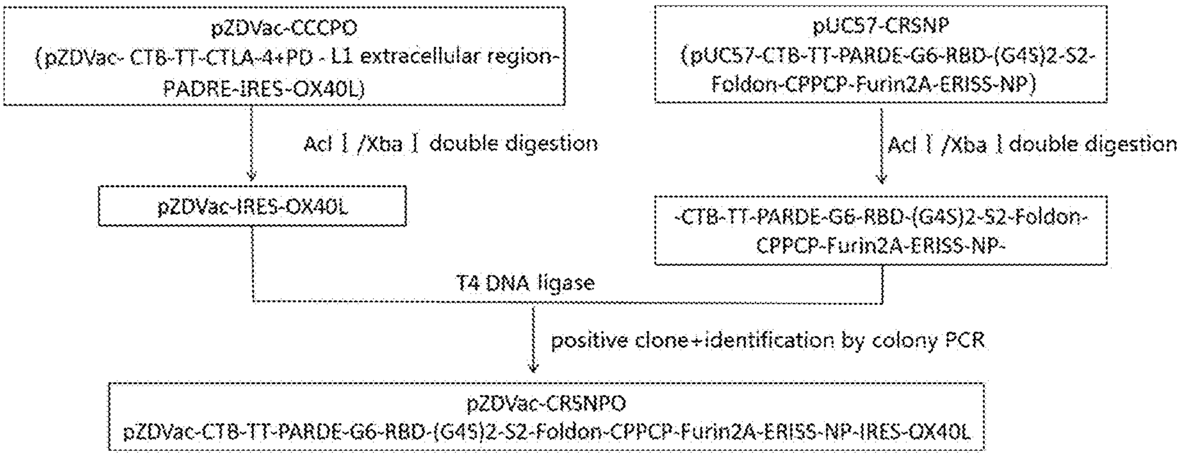
FIG. 5 is a construction schematic diagram of recombinant plasmid pZDVac-CRSNPO.

1.3. Construction of Recombinant Novel Coronavirus High-Efficiency Immune DNA Vaccine As shown in FIG. 5, the expression vector backbone pZDVac-IRES-OX40L obtained in the above step 1.1 was connected to the first target gene CRSNP obtained in the step 1.2 by T4 ligase, and the recombinant expression vector carrying the first target gene fragment CRSNP was obtained by colony PCR to screen positive clone: pZDVac-CTB-TT-PARDE-G6-RBD-$(G4S)_2$-S2-Foldon-CPPCP-Furin2A-ERISS-NP-IRES-OX4 0L (named pZDVac-CRSNPO recombinant plasmid, wherein the nucleotide sequence corresponding to fusion gene CTB-TT-PARDE-G6-RBD-$(G4S)_2$-S2-Foldon-CPPCP-Furin2A-ERISS-NP-IRES-OX40L is set forth in SEQ ID NO:13, in addition to the nucleotide sequences shown in Table 1 above, it also contains restriction sites). The recombinant expression vector was the recombinant novel coronavirus high-efficiency immune DNA vaccine ZD-nCor19, and the specific construction steps included:

1.3.1. T4 Ligation

The expression vector backbone pZDVac-IRES-OX40L (about 12 kb) obtained by the gel recovery in the above step 1.1 was connected to the first target gene fragment CRSNP (about 3.6 kb) obtained by the gel recovery in the step 1.2, and the ligation product was obtained overnight at 16° C. The system was shown in Table 2.

TABLE 2

| T4 ligation system | |
|---|---|
| Reagents Name | Dosage |
| Expression vector backbone pZDVac-IRES-OX40L | 4 μL (20 ng) |
| First target gene fragment CRSNP | 8 μL (600 ng) |
| ligase 10 × NEB buffer | 2 μL |
| T4 DNA ligase | 2 μL (200 U) |
| $ddH_2O$ | 4 μL |
| Total volume | 20 μL |

1.3.2. Screening of Positive Clones

100 μL of stable competent cells were placed in an ice bath. After the competent cells were thawed, 10 μL of the ligation product obtained in the above step 1.3.1 was added into the competent cell suspension, mixed gently, and placed in an ice bath for 30 minutes, then immediately transferred to a 42° C. water bath for heat shock for 90 s, and then quickly transferred to an ice bath for 2 min. 500 μL of sterile antibiotic-free LB medium was added to the transformed cells, mixed evenly, and then incubated with shaking at 150 rpm for 60 min at 37° C., and then centrifuged at 12,000 rpm for 1 min, and 500 μL of supernatant was discarded. 100 μL of transformed cells were taken and evenly spread on LB agar plate containing kanamycin (50 μg/mL), and cultured at 37° C. for 48 hours in an inverted petri dish.

Figure 6:
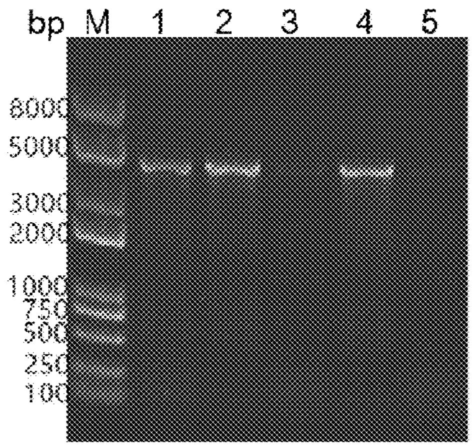
FIG. 6 is a gel electrophoresis photograph showing identification of positive clones by colony PCR.

Single colonies were picked and screened positive clones by colony PCR. Upstream primer F and downstream primer R were designed for PCR amplification (primer sequences were synthesized by Beijing Biomed):

Upstream primer F:
(SEQ ID NO: 14)
CCCAGGAGACCCGGTTCTAGAGACGGACATT;

Downstream primer R:
(SEQ ID NO: 15)
AAGCGGCTTCGGCCAGTAACGTTAGGGGGGG;

The PCR system (25 μL) was: 12.5 μL of 2×PCR mix (purchased from Beijing Biomed); 11.5 μL of $ddH_2O$; 0.5 μL of F (10 μM) and 0.5 μL of R (10 μM). The PCR reaction conditions for PCR amplification of the ligation product transformed colonies were 95° C. for 5 min, 1 cycle; 94° C. for 30 s, 55° C. for 30 s, and 72° C. for 50 s, 35 cycles; and 72° C. for 7 min. PCR products were analyzed by 0.45% agarose DNA gel electrophoresis, and the results were shown in FIG. 6, where in Lanes 1-5 were PCR results of different single colonies.

1.3.3. Plasmid Extraction and Restriction Enzyme Digestion Identification of Positive Clones Positive colonies screened by colony PCR were streaked on LB agar plate containing kanamycin (50 μg/mL) and cultured overnight at 37° C. in an inverted petri dish. Then a single clone was picked and inoculated in 1.5 mL LB medium containing kanamycin (50 μg/mL),cultured overnight at 37° C. and 200 rpm, then the obtained bacterial liquid was inoculated in 20 mL LB medium containing kanamycin (50 μg/mL) at a ratio of 1:50, and cultured overnight at 37° C. and 200 rpm. In a sterile environment, 12 mL of the bacterial liquid was taken and prepared into glycerol bacteria based on the ratio of 1.2 mL bacterial liquid+0.6 mL of 60% glycerol. The remaining bacterial liquid was centrifuged to extract plasmids, which were identified by single and double digestion with AclI and XbaI respectively. The single and double digestion systems were shown in Tables 3 and 4 below.

TABLE 3

Single digestion system

| Reagents Name | Dosage |
|---|---|
| Plasmid extracted from a positive clone | 7 μL |
| restriction enzyme AclI or XbaI | 0.5 μL |
| Cutsmart (10×) | 2 μL |
| $ddH_2O$ | 10.5 μL |
| Total volume | 20 μL |

TABLE 4

Doubledigestion system

| Reagents Name | Dosage |
|---|---|
| Plasmid extracted from a positive clone | 7 μL |
| restriction enzyme AclI or XbaI | 0.5 μL + 0.5 μL |
| Cutsmart (10×) | 2 μL |
| $ddH_2O$ | 10 μL |
| Total volume | 20 μL |

Figure 7:
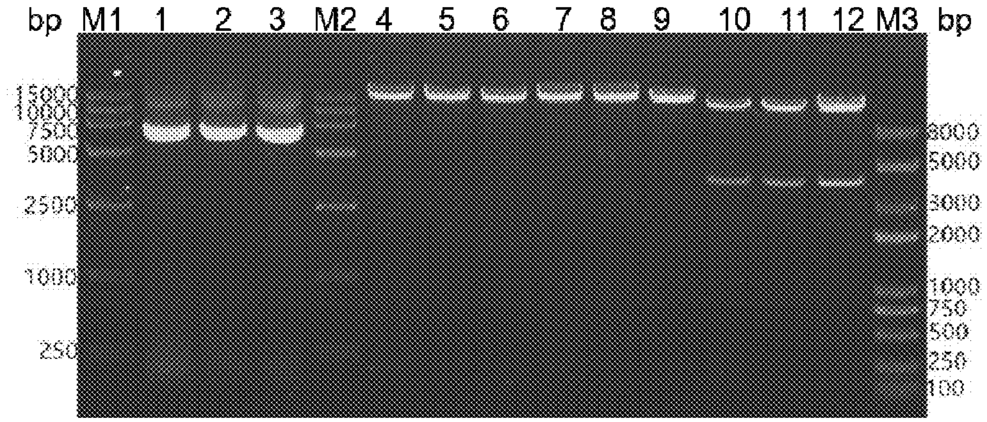
FIG. 7 is a gel electrophoresis photograph showing digestion identification of the plasmid extracted from positive clones on a small amount.

The samples were mixed according to the enzyme digestion system in Table 3 or 4 above, and centrifuged briefly to allow the sample and enzyme(s) to sink to the bottom of the tube. The centrifuge tubes were placed in a 37° C. water bath and incubated for 2 h. The bands of the expected size were identified by 0.45% agarose gel electrophoresis, and the identification results were shown in FIG. 7, wherein Lanes 1-3 were the results of plasmids from the positive clones 1, 2, and 4 screened by colony PCR in FIG. 6, respectively; Lanes 4-6 were the results of AclI single digestion of plasmids from the positive clones 1, 2, and 4, respectively; Lanes 7-9 were the results of XbaI single digestion of plasmids from the positive clones 1, 2 and 4, respectively; Lanes 10-12 were the results of AclI and XbaI double digestion of plasmids from the positive clone 1, 2 and 4, respectively, including a band of about 12 kb in size and a band of about 3.6 kb in size, which proved that the recombinant plasmid pZDVac-CRSNPO, namely recombinant novel coronavirus high-efficiency immune DNA vaccine, was constructed.

In this example, a recombinant plasmid pZDVac-RBD-$(G4S)_2$-S2-NP (in which the empty vector pZDVac was used as the backbone vector, named as Control Plasmid 1) carrying the second target gene (RBD-$(G4S)_2$-S2-NP), and the recombinant plasmid pZDVac-Foldon-CPPCP-TT-PARDE-G6-RBD-$(G4S)_2$-S2-CTB-Furin2A-ERISS-NP-IRES-OX4 0L (named as Control plasmid 2) carrying the third target gene (Foldon-CPPCP-TT-PARDE-G6-RBD-$(G4S)_2$-S2-CTB-Furin2A-ERISS-NP) were constructed in the way similar as the way in step 1.3.

EXAMPLE 2

Immunogenicity Induced by pZDVac-CRSNPO Recombinant Plasmid in Mouse Model

In this example, the pZDVac-CRSNPO recombinant plasmid constructed and obtained in the above Example 1 was used to verify its immunogenic effect induced in the mouse model, specifically including the following steps.

2.1. Twenty 6-8-week-old SPF female BALB/c mice (purchased from Beijing Weitong Lihua Laboratory Animal Technology Co., Ltd.) were randomly divided into 4 groups, with 5 mice in each group, and were immunized 3 times by intramuscular injection+electrical pulse stimulation, and the immunization interval was 7 days. The experimental groups and doses are shown in Table 5.

TABLE 5

Grouping of pZDVac-CRSNPO recombinant plasmid in mouse model cellular immune response detection experiments

| Group | Vaccine plasmid | Immunizing dose | Vaccination strategies | Number of animals |
|---|---|---|---|---|
| Bland Group | PBS | 100 μL | intramuscular injection + electrical pulse stimulation | 5 mice/group |
| Group 0.3 μg | pZDVac-CRSNPO | 0.3 μg/100 μL | | |
| Group 1 μg | pZDVac-CRSNPO | 1 μg/100 μL | | |
| Group 10 μg | pZDVac-CRSNPO | 10 μg/100 μL | | |

2.2. 2 weeks after the last immunization, the mice were sacrificed, and the spleen lymphocytes were isolated. After culturing for 20 hours with the stimulation of the N protein and RBD protein of the novel coronavirus, immunology detection was performed according to the instructions of MabTech's Mouse IFN-γ and IL-4 ELISPOT plates. The statistical results of the secretion frequency detection of cytokines IFN-γ and IL-4 under different protein stimulators were shown in FIG. 8 and FIG. 9 respectively (where $p<0.05$ is statistically significant). The statistical results of antigen-specific T cell immune response bias were shown in FIG. 10.

Figure 8:
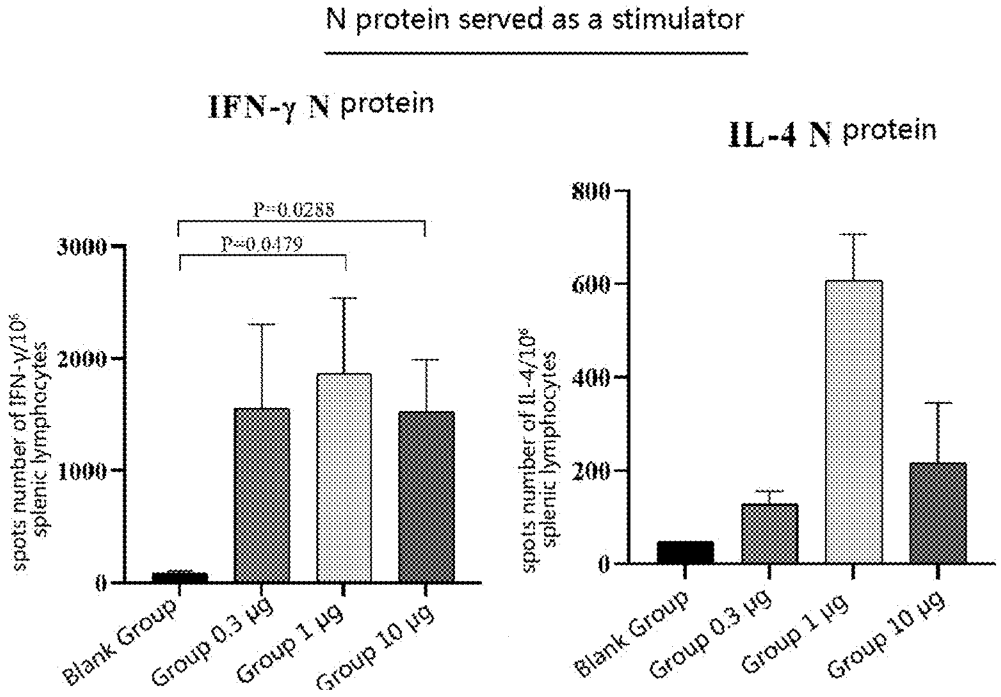
FIG. 8 is a bar graph of the secretion frequency of cytokines IFN-γ and IL-4 in mouse spleen cells with N protein as a stimulator after immunizing mice with recombinant plasmid pZDVac-CRSNPO.
Figure 9:
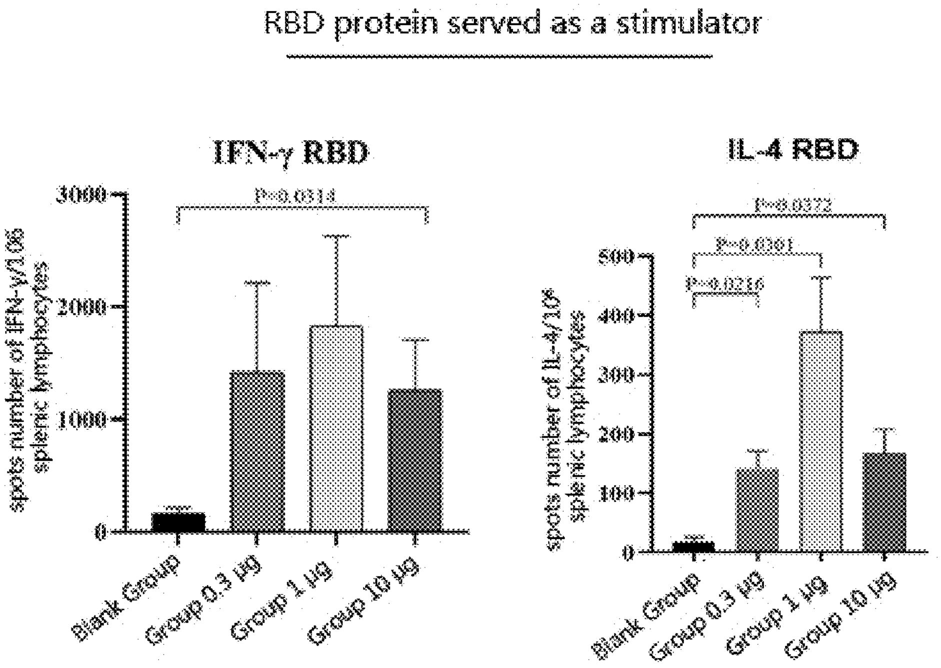
FIG. 9 is a bar graph of the secretion frequency of cytokines IFN-γ and IL-4 in mouse spleen cells with RBD protein as a stimulator after immunizing mice with recombinant plasmid pZDVac-CRSNPO.
Figure 10:
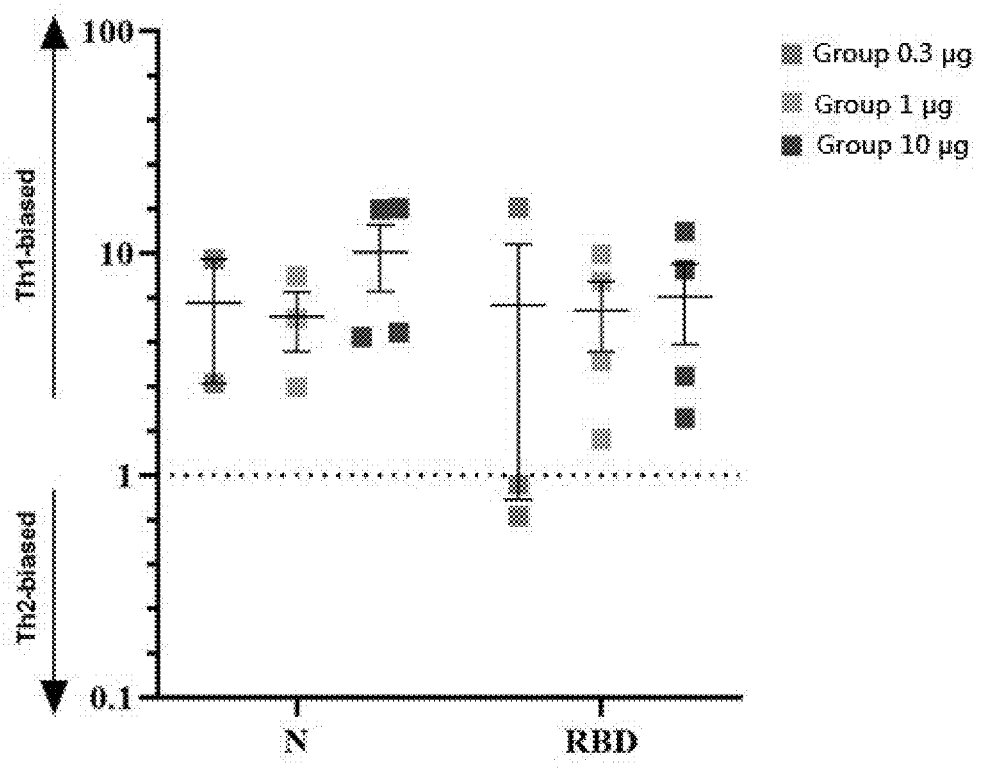
FIG. 10 is a scatter plot of the type bias analysis of T cell responses induced by recombinant plasmid pZDVac-CRSNPO in a mouse model.

The results shown in FIG. 8 to FIG. 10 showed that different doses of pZDVac-CRSNPO recombinant plasmid could induce N antigen and RBD antigen-specific T cell immune responses in mice after immunization, and secrete not only IFN-γ representing Th1-type response, but also IL-4 representing Th2-type response, wherein the secretion frequency of Th1-type cytokine IFN-γ was significantly higher than that of Th2-type cytokine IL-4. The results indicated that the T cell immune response induced by the pZDVac-CRSNPO recombinant plasmid was biased towards Th1, and compared with Group 0.3 μg and Group 10 μg, 1 μg was the optimal immune dose.

According to the same method as shown in the above steps 2.1 and 2.2, the immunogenicity induced by immunization of 6-8-week-old SPF female BALB/c mice with Control plasmid 1 and Control plasmid 2 was detected respectively. The results showed that the immunogenic effect induced by Control plasmid 1 and Control plasmid 2 was not as good as that induced by the pZDVac-CRSNPO recombinant plasmid.

EXAMPLE 3

Immunogenicity Detection of pZDVac-CRSNPO Recombinant Plasmid in Humans

In this example, the pZDVac-CRSNPO recombinant plasmid constructed and obtained in Example 1 was used to immunize human subjects, and the immunogenicity effect induced in the human body was verified, including the following steps.

3.1. 15 selected volunteers (internal personnel of the applicant unit, who have signed to volunteer to participate in the trial) were randomly divided into 3 groups with 5 people in each group. The immunization interval was 28 days, and the immunization was carried out three times. Before the first immunization, 14 days after the second immunization and 21 days after the third immunization, PBMCs from the volunteers were taken for ELISPOT detection. The first two immunizations were intramuscular injection+electrical pulse stimulation, and the third immunization was intradermal injection+electrical pulse stimulation. The experimental groups and doses are shown in Table 6 below.

TABLE 6

Grouping of pZDVac-CRSNPO recombinant plasmid in the detection of cellular immune response in human subjects

| Group | Vaccine plasmid | Immunizing dose | Number of volunteers |
|---|---|---|---|
| Low dose group | pZDVac-CRSNPO | 100 μg | 5 persons/group |
| Medium dose group | | 300 μg | |
| High dose group | | 500 μg | |

3.2. The fresh PBMCs obtained from the volunteers were taken, and stimulated and cultivated with N protein and RBD protein of the novel coronavirus for 20 hours, and immunological detection was performed according to the instructions of Human IFN-γ ELISPOT plates of MabTech Company. The statistical results of the secretion frequency detection of cytokine IFN-γ under different protein stimulators after three immunizations were shown in FIG. 11 (wherein $p<0.05$ means the statistical difference is significant; $p<0.01$ means the statistical difference is very significant). The statistical results of the three immunizations responses with different dose were shown in FIG. 12 (wherein $p<0.05$ means that the statistical difference is significant; $p<0.01$ means that the statistical difference is very significant).

Figure 11:
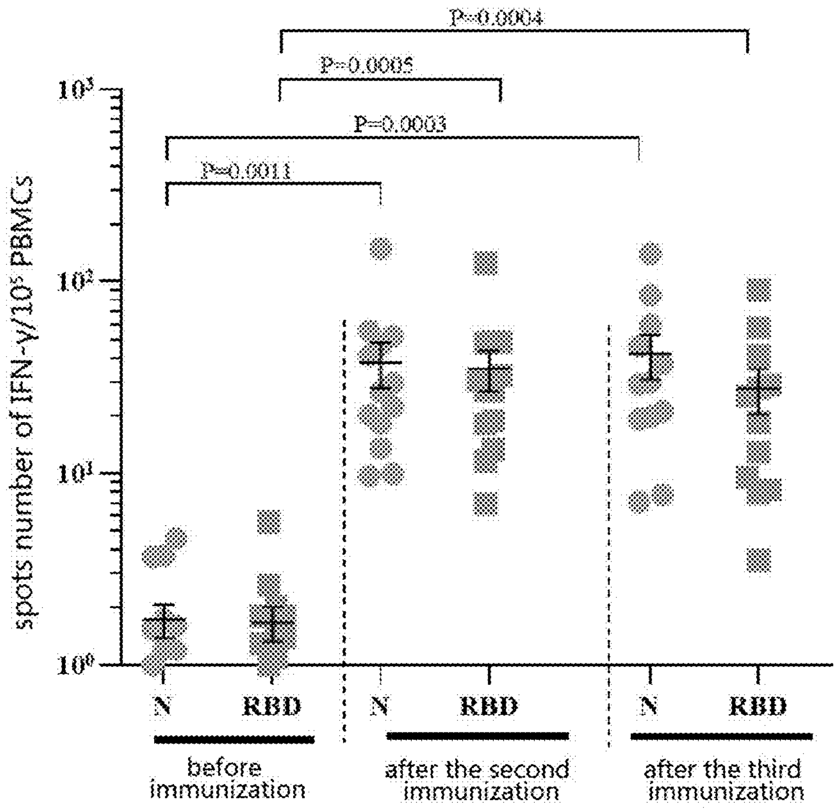
FIG. 11 is a scatter plot of the secretion of cytokine IFN-γ in human PBMCs with N protein and RBD protein as stimulators before and after immunization of human subjects with recombinant plasmid pZDVac-CRSNPO.
Figure 12:
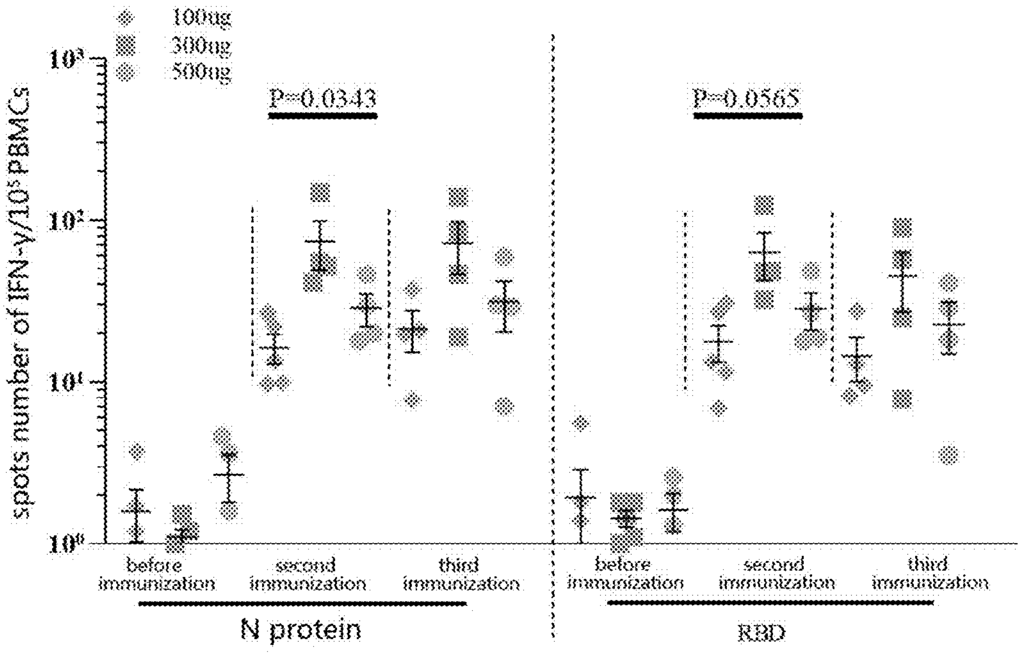
FIG. 12 is a scatter plot of the secretion of cytokine IFN-γ in human PBMCs with N protein and RBD protein as stimulators before and after immunization of human subjects with recombinant plasmid pZDVac-CRSNPO at different doses.

The results in FIG. 11 showed that compared with that before immunization, strong cellular immune responses could be induced after secondary and tertiary immunization, and the secretion frequency of cytokine IFN-γ in PBMCs had very significant increase when N protein and RBD protein were used as stimulators, respectively; and the secretion frequency of the cytokine IFN-γ after the third immunity was higher than that after the second immunity when the N protein was used as a stimulator, and the secretion frequency of the cytokine IFN-γ after the second immunity was higher than that after the third immunity when the RBD protein was used as a stimulator. The results in FIG. 12 showed that the number of spots in different dose groups increased significantly after immunization compared with that before immunization, indicating that specific cellular immunity could be effectively induced at each dose; while there were significant difference ($p=0.0343$, which is the result of variance analysis among the three dose groups of low, medium and high doses) in the number of spots among the dose groups after the second immunization when N protein and RBD protein was used as a stimulator. It could be seen that compared with the high-dose group and the low-dose group, the immune effect of the medium-dose group was better, and the number of spots did not increase much after the third immunization. Therefore, when the pZDVac-CRSNPO recombinant plasmid is used as a new coronavirus DNA vaccine, 2 immunizations at medium-dose (for example, 28 days between 2 immunizations) can be used.

In addition, the 15 volunteers screened in this example underwent regular follow-up and physical examination (at least 3 months) after the vaccine injection, and all volunteers did not show any discomfort, which preliminarily shows that the pZDVac-CRSNPO recombinant plasmid provided by the present invention has a good safety profile when used as a vaccine.

EXAMPLE 4

Immune Routes and Electro-Introduction Conditions of pZDVac-CRSNPO Recombinant Plasmid In this example, the pZDVac-CRSNPO recombinant plasmid constructed and obtained in Example 1 was used to immunize mice through different immunization routes (intramuscular injection or intradermal injection) and under different electro-introduction conditions to evaluate the intensity of the immune response induced through different immunization routes and under the different electro-introduction conditions, specifically including the following steps.

4.1. According to the groups shown in Table 7 below, 40 healthy 6-8-week-old female Balb/c mice (purchased from Viton Lever) were randomly divided into 5 groups, 8 mice in each group, respectively. The mice in each group were immunized by single-point administration to the left hind limb of mice by means of intramuscular injection or intradermal injection &electro-introduction (1 Hz×6 times, 0.5 cm of electrode needle spacing), respectively. A blank control group was set without treatment, and mice in other groups were given 1 μg/mice of pSFVK1-CRSNPO recombinant plasmid. The dosing day was counted as 0 d, and 5 groups of mice were immunized twice on 0 d and 21 d respectively.

TABLE 7

Grouping of mice under different immunization routes and electro-introduction conditions of pZDVac-CRSNPO recombinant plasmid

| Group | voltage | pulse width |
|---|---|---|
| Blank control group | — | — |
| Intramuscular injection group | 60 V | 50 ms |
| Intradermal injection group a | 60 V | 50 ms |
| Intradermal injection group b | 36 V | 50 ms |
| Intradermal injection group c | 36 V | 10 ms |

4.2. The serum was taken 2 weeks after the last immunization for antibody detection. Specifically, ACRO Biosystems antibody detection kit for serum antibody (RBD IgG)

detection was used. The mouse serum was diluted at 1:100, and positive judgment was the absorbance value at OD450 nm>0.1.2 weeks after the last immunization, mice in each group were sacrificed, and ELISPOT detection (IFN-γ) was performed according to the instructions of MabTech's IFN-γ ELISPOT plate. The expression method of spot count in ELISPOT experiment was: spot-forming units (SFU)/$10^6$ splenocytes; the criteria for judging the experimental wells as positive was: the number of spots in the experimental wells>the average spot value of the negative control wells+2SD; the calculation method for the number of positive spots in each mouse was as follows: 5 duplicate wells were made for the spleen cells of one mouse, and if at least 3 wells were positive, then the data of this mouse would be valid, and the number of spots in this mouse=the average number of spots in experimental wells−the number of spots in the negative control wells; the calculation method of the number of spots in each group of mice was as follows: the data of each effective mouse in the group was averaged and expressed as the mean±standard deviation. Statistical analysis of the data was performed with GraphPad Prism 8 software, wherein the differences between two groups were analyzed with Student's t test, and the differences among multiple groups were compared with one-way analysis of variance. $p<0.05$ means that the difference is statistically significant, and $p<0.01$ means that the difference is very significant.

Figure 13:
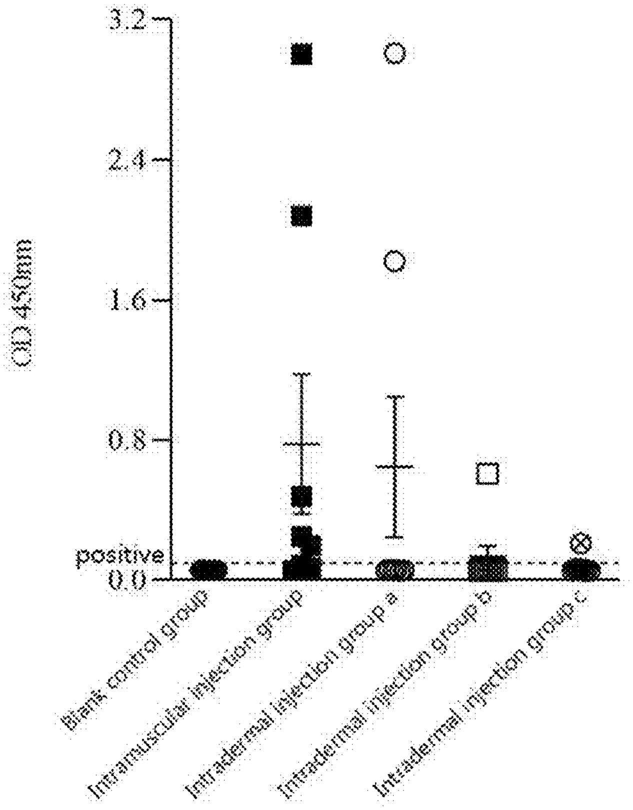
FIG. 13 is a scatter diagram of the detection results of antibodies induced by using the recombinant plasmid pZDVac-CRSNPO to immunize mice under different immunization routes and different electro-introduction conditions.

The results of antibody detection were shown in FIG. 13. It could be seen that the pSFVK1-CRSNPO recombinant plasmid can induce antibody responses after immunizing mice through different routes (intramuscular injection and intradermal injection) or under different electro-introduction conditions. Compared with the blank control group, the antibody level induced by the intramuscular injection group (60V, 50 ms, 1 Hz×6 times, 0.5 cm of electrode needle spacing, and 120V/cm of field strength) was statistically different; the antibody level induced by the intradermal injection group a (60V, 50 ms, 1 Hz×6 times, 0.5 cm of electrode needle spacing, 120V/cm of field strength) was also statistically significantly different from that of the blank control group; while the antibody levels induced by the intradermal injection group b (36V, 50 ms), and c (36V, 10 ms) had no statistically significant difference compared with the blank control group. These results showed that under the conditions of intramuscular injection and subcutaneous injection, compared with the electro-introduction conditions with voltage of 36V, and pulse width of 50 ms, it had a relatively better immune effect when the electro-introduction conditions were 60V of voltage, 50 ms of pulse width. In addition, under the same electro-introduction conditions, the antibody level induced by intradermal injection group a was not statistically different from that of intramuscular injection group, but in general, immunization with pSFVK1-CRSNPO recombinant plasmid through intramuscular injection route had relatively better humoral immunity effect.

Figure 14:
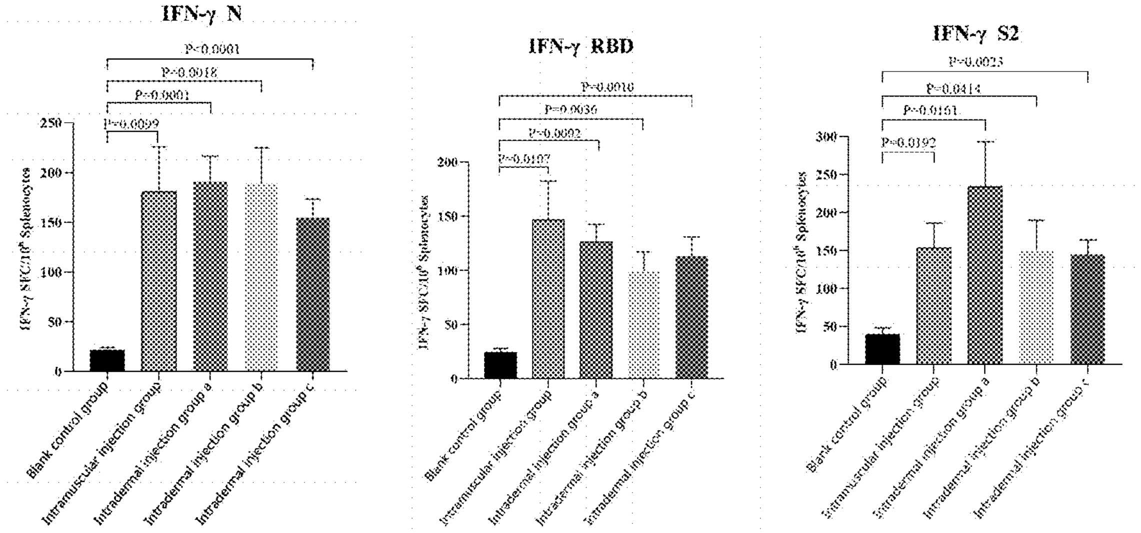
FIG. 14 is a bar chart of the Elispot assay results of N antigen, RBD antigen and S2 antigen induced after immunizing mice with recombinant plasmid pZDVac-CRSNPO under different immunization routes and different electro-introduction conditions.

The ELISPOT test results were shown in FIG. 14. It could be seen that the pSFVK1-CRSNPO recombinant plasmid could induce N antigen, RBD antigen and S2 antigen-specific T cell immune responses after immunizing mice with different routes (intramuscular injection and intradermal injection) and under different electro-introduction conditions. The experimental groups (intramuscular injection group, subcutaneous injection group a, b, c) were all statistically significantly different from the blank control group. Among them, the N antigen, RBD antigen and S2 antigen-specific T cells immune responses induced by immunization by intradermal injection under various electro-introduction conditions were different from those by immunization by intramuscular injection.

To sum up, the results showed that the pSFVK1-CRSNPO recombinant plasmid vaccine provided by the present invention could induce strong specific T cell immune responses in mice stimulated through different immunization routes and under different electro-introduction conditions, and there was no significant difference in the induced cellular immune response between the intramuscular injection group and the intradermal injection group. The pSFVK1-CRSNPO recombinant plasmid vaccine provided had a relatively better induction effect in terms of inducing humoral immune response under the conditions of voltage 60V and pulse width 50 ms, and in general, vaccine administered intramuscularly produced relatively better humoral immune response. Therefore, the pSFVK1-CRSNPO recombinant plasmid provided by the present invention can induce a good cellular immune response and humoral immune response when used as a vaccine, and can exert a good protective effect of vaccination, which is consistent with the results of Examples 2 and 3 above.

EXAMPLE 5

Immune Challenge Test

In this example, according to the vaccine immunization method in the above-mentioned Example 4 (intramuscular injection or subcutaneous injection &electro-introduction (60V, 50 ms, 1 Hz×6 times, 0.5 cm of electrode needle spacing, 120V/cm of field strength)), pSFVK1-CRSNPO recombinant plasmid was used to immunize hACE2 transgenic mice or rhesus monkeys, and a negative control group was set up and given normal saline. The dosing day was counted as 0 d, and the animals in each group were immunized twice on 0 d and 21 d respectively, and the animals in each group were challenged (novel coronavirus liquid) 2 weeks after the last immunization. The reduction of pulmonary viral load and the pulmonary pathological conditions of the animals in each group were investigated, and the reduction of pulmonary viral load (≥2 logs) and the improvement of pulmonary pathology were the basic requirements for effectiveness evaluation. The results showed that the animals in the negative control group showed typical clinical symptoms of novel coronavirus infection (such as fever, lethargy, weight loss, and even death) after the challenge, while at least 4/5 of the animals in the immunized group were protected, without showing any of typical clinical symptoms of novel coronavirus infection, and the pulmonary viral load reduced (≥2 logs) and the pulmonary pathology was significantly improved. These results show that the recombinant novel coronavirus high-efficiency immune DNA vaccine ZD-nCor19 provided by the present invention has effectiveness and safety.

To sum up, the results of the above examples showed that the recombinant novel coronavirus high-efficiency immune DNA vaccine (that is, the pZDVac-CRSNPO recombinant plasmid) constructed and obtained by the present invention can effectively induce high-efficiency immune responses in animal-level immunological function tests, including natural immune responses and antigens-specific cellular immune response, which proves that it is a new type of coronavirus DNA vaccine with great development potential. After using the vaccine to immunize human subjects, it was found that it could induce high levels of natural immune responses and antigen-specific cellular immune responses in all three dose groups (100 μg, 300 μg, 500 μg), and the highest level of immune response was induced in the 300 μg dose group. All human subjects who participated in the test did not have any obvious adverse reactions such as fever, allergy, headache, general weakness, etc. during regular follow-up and physical examination. By comparing the strength of the immune response induced through different immunization routes and under different electro-introduction conditions, it shows that the recombinant novel coronavirus high-efficiency immune DNA vaccine provided by the present invention can be inoculated through intramuscular injection and subcutaneous injection, and both can induce good specific T cell immune responses and humoral immune responses. The results of the immune challenge test also shows that the recombinant novel coronavirus high-efficiency immune DNA vaccine of the present invention has good safety and immune protection effects. The above results all preliminarily confirm that the vaccine constructed by the present invention is a kind of vaccine that can induce high-level immune response and at the same time is very mild and safe.

The examples described herein are for illustration (as an example) only, and various modifications or changes made by the skilled person should also be included within the essential scope of the patent application.

INDUSTRIAL APPLICABILITY

The present invention provides a fusion gene and a recombinant novel coronavirus high-efficiency immune DNA vaccine based on the fusion gene and a construction method and use thereof, wherein the recombinant novel coronavirus high-efficiency immune DNA vaccine has the dual effects of preventing and treating novel coronavirus infection, suitable for industrial applications.

The invention claimed is:

1. An isolated fusion gene, comprising the following (1) to (4):

(1) a gene expressing the severe acute respiratory syndrome coronavirus type 2 (SARS CoV-2) spike(S) protein receptor binding domain (RBD), wherein the nucleotide sequence of the gene is set forth in nucleotides 1-669 of SEQ ID NO:6;

(2) a gene expressing amino acid residues 301-538 of SARS COV-2 S protein S2 subunit, wherein the nucleotide sequence of the gene is set forth in nucleotides 700-1413 of SEQ ID NO: 6;

(3) a gene expressing amino acid residues 138-369 of the SARS COV-2 N protein, wherein the nucleotide sequence of the gene is set forth in SEQ ID NO: 10; and (4) a nucleic acid sequence encoding or comprising at least one of the following: cholera toxin B subunit (CTB), tetanus toxin helper T cell epitope (TT), pan-DR helper T cell epitope (PADRE), Foldon, CPPCP (SEQ ID NO:16), Furin2A, endoplasmic reticulum insertion signal sequence (ERISS), internal ribosome entry site (IRES), and OX40L.

2. The fusion gene of claim 1, wherein the gene expressing the SARS CoV-2 S protein RBD and the gene expressing the amino acid residues 301-538 of SARS CoV-2 S protein S2 subunit are linked to form a gene for expressing a fusion protein (RBD-S2).

3. The fusion gene of claim 1, wherein:

(1) the nucleotide sequence of the gene expressing the CTB is set forth in SEQ ID NO: 2;

(2) the nucleotide sequence of the gene expressing the TT is set forth in SEQ ID NO: 3;

(3) the nucleotide sequence of the gene expressing the PADRE is set forth in SEQ ID NO: 4;

(4) the gene expressing the Foldon and the gene expressing the CPPCP (SEQ ID NO:16) are linked to form a synthetic fragment, and the nucleotide sequence of the synthetic fragment is set forth in SEQ ID NO:7;

(5) the nucleotide sequence of the gene expressing the Furin2A is set forth in SEQ ID NO: 8;

(6) the nucleotide sequence of the gene expressing the ERISS is set forth in SEQ ID NO: 9;

(7) the nucleotide sequence of the gene expressing the IRES is set forth in SEQ ID NO: 11;

(8) the nucleotide sequence of the gene expressing the OX40L is set forth in SEQ ID NO: 12.

4. The fusion gene of claim 1, wherein the fusion protein obtained from the expression of the fusion gene comprises, in the N-to C-terminal orientation, CTB-TT-PADRE-RBD-S2-Foldon-CPPCP-Furin2A-ERISS-N protein-IRES-OX40L;

wherein S2 is the amino acid residues 301-538 of SARS COV-2 S protein S2 subunit, and wherein N protein is the amino acid residues 138-369 of the SARS COV-2 N protein.

5. A fusion protein obtained from the expression of the fusion gene of claim 1.

6. A recombinant novel coronavirus immune DNA vaccine (ZD-nCor19) comprising the fusion gene of claim 1, wherein said gene is present within a vector.

7. The recombinant novel coronavirus immune DNA vaccine of claim 6, wherein the vector is pZDVac vector.

8. A method for constructing a recombinant novel coronavirus immune DNA vaccine, comprising the following steps of:

1) synthesizing the fusion gene of claim 1;

2) inserting the fusion gene into a pZDVac vector to obtain the recombinant novel coronavirus immune DNA vaccine.

9. A method for inhibiting infection from SARS Cov-2, or treatment/prevention of disease associated with a SARS COV-2 infection, comprising administering an effective amount of the recombinant novel coronavirus immune DNA vaccine of claim 6 to a subject infected with SARS COV-2 or at risk of SARS COV-2 infection.

10. The fusion gene of claim 2, wherein the nucleotide sequence of the gene for expressing the fusion protein RBD-S2 comprises the sequence set forth in SEQ ID NO: 6.

11. The fusion gene of claim 2, wherein the gene expressing the SARS CoV-2 S protein RBD and the gene expressing the amino acid residues 301-538 of the SARS CoV-2 S protein S2 subunit are linked by a gene expressing a (G4S) 2 linker.

12. The fusion gene of claim 4, wherein the gene expressing the SARS CoV-2 S protein RBD and the gene expressing the amino acid residues 301-538 of the SARS CoV-2 S protein S2 subunit are linked by a gene expressing a (G4S) 2 linker, the gene expressing the SARS COV-2 S protein RBD and the gene expressing the PADRE are linked by the-a gene expressing a linker G6, and the nucleotide sequence of the gene expressing the linker G6 is set forth in SEQ ID NO:5.

13. The fusion gene of claim 1, wherein the nucleotide sequence of the fusion gene is set forth in SEQ ID NO:13.

14. The method of claim 8, wherein the fusion gene synthesized in step 1) comprises the following (1) to (4):

(1) a gene expressing the SARS COV-2 S protein RBD;

(2) a gene expressing amino acid residues 301-538 of the S2 subunit of SARS COV-2 S protein;

(3) a gene expressing amino acid residues 138-369 of the SARS COV-2 N protein;

(4) genes expressing the following proteins: CTB, TT, PADRE, Foldon, CPPCP, Furin2A, ERISS, IRES and OX40L;

wherein the gene expressing the SARS COV-2 S protein RBD and the gene expressing the amino acid residues 301-538 of the S2 subunit of SARS COV-2 S protein are linked to form a gene for expressing a fusion protein (RBD-S2), and wherein said RBD and the amino acid residues 301-538 of the S2 subunit are joined by a (G4S) 2 linker;

wherein upstream of the fusion protein RBD-S2, CTB, TT, and PADRE are sequentially linked, and wherein downstream of the fusion protein RBD-S2, foldon, CPPCP, and Furin2A are sequentially linked;

wherein the gene expressing ERISS is linked upstream of said amino acid residues 138-369 of the SARS COV-2 N protein; and wherein downstream of said amino acid residues 138-369 of the SARS COV-2 N protein, genes encoding IRES and OX40L are sequentially linked; and wherein the gene expressing PADRE and the gene for expressing the fusion protein RBD-S2 are linked by a G6 linker (SEQ ID NO:5).

15. The method of claim 8, wherein the nucleotide sequence of the fusion gene synthesized in step 1) is set forth in SEQ ID NO:13.

* * * * *